US006004781A

United States Patent [19]
Seed

[11] Patent Number: 6,004,781
[45] Date of Patent: Dec. 21, 1999

[54] NUCLEIC ACID ENCODING IG-CD4 FUSION PROTEINS

[75] Inventor: Brian Seed, Boston, Mass.

[73] Assignee: The General Hospital Corporation, Charlestown, Mass.

[21] Appl. No.: 08/191,708

[22] Filed: Feb. 4, 1994

Related U.S. Application Data

[63] Continuation of application No. 08/057,952, Apr. 12, 1993, abandoned, which is a continuation of application No. 07/896,781, Jun. 9, 1992, abandoned, which is a continuation of application No. 07/299,596, Jan. 23, 1989, abandoned, which is a continuation-in-part of application No. 07/147,351, Jan. 22, 1988, abandoned.

[51] Int. Cl.$^6$ ..................................................... C12N 15/62
[52] U.S. Cl. .................. 435/69.7; 435/252.3; 435/320.1; 536/23.4
[58] Field of Search ............................... 435/69.7, 252.3, 435/320.1; 536/23.4

[56] References Cited

U.S. PATENT DOCUMENTS

| 4,675,382 | 6/1987 | Murphy | 530/350 |
| 4,816,567 | 3/1989 | Cabilly et al. | 530/387 |
| 5,336,603 | 8/1994 | Capon et al. | 435/69.7 |

FOREIGN PATENT DOCUMENTS

| 0 120 694 | 10/1984 | European Pat. Off. . |
| 0 125 023 | 11/1984 | European Pat. Off. . |
| 0314317 A1 | 5/1989 | European Pat. Off. . |
| WO88/01304 | 2/1988 | WIPO . |
| WO89/01940 | 3/1989 | WIPO . |
| WO89/02922 | 4/1989 | WIPO . |

OTHER PUBLICATIONS

Deen, K.C., et al., "A soluble form of CD4 (T4) protein inhibits AIDS virus infection," Nature 331:82–84 (Jan. 7, 1988).
Fisher, R.A., et al., "HIV infection is blocked in vitro by recombinant soluble CD4," Nature 331:76–78 (Jan. 7, 1988).
Article entitled "Prevention of HIV–1 IIIB Infection in Chimpanzees by CD4 Immunoadhesin" by Ward et al., Nature, 352:434–436 (1991).
Article entitled "Prevention of HIV–2 and SIVsm Infection by Passive Immunization in Cynomolgus Monkeys" by Putkonen et al., Nature 352:436–438 (1991).
Mizukami, T., et al., "Expression and Characterization of Chimeric Proteins Containing Human CD4 Linked to Human Immunoglobulin Heavy Chain Constant Regions," in Morisset, R.A. (ed.) V International Conference on AIDS, Abstract No. M.C.P. 89 (Montreal, Canada 1989), p. 556.
Morrison, et al., "Chimeric human antibody molecules: Mouse antigen–binding domains with human constant region domains," Proc. Natl. Acad. Sci. USA 81:6851–6855, 1984.
McDougal, et al., "Binding of HTLV–III/LAV to T4+ T Cells by a Complex of the 110K Viral Protein and the T4 Molecule," Science 231:382–385, 1986.

Maddon, et al., "The Isolation and Nucleotide Sequence of a cDNA Encoding the T Cell Surface Protein T4: A New Member of the Immunoglobulin Gene Family," Cell 42:93–104, 1985.
Capon, et al., "Designing CD4 Immunoadhesine for AIDS Therapy," Nature 337:525–531 1989.
Gascoigne, N.R.J. et al., "Scretion of a Chimeric T–cell Receptor–immunoglobulin protein," Proc. Natl. Acad. Sci. (USA) 84:2936–2940 (1987).
Lasky, L. A. et al., "Delineation of a Region of the Human Immuno–deficiency Virus Type 1 gp120 Glycoprotein Critical for Interaction with the CD4 Receptor," Cell 50:975–985 (1987).
Traunecker, A. et al., "Soluble CD4 Molecules Neutralize Human Immuno–deficiency Virus Type 1," Nature 331:84–86 (1988).
Kowalski, M. et al., "Functional Regions of the Envelope Glycoprotein of Human Immunodeficiency Virus Type I," Science 237:1351–1355 (1987).
Stricker, et al., "An AIDS–related Cytotoxic Autoantibody Reacts with a Specific Antigen on Stimulated CD4+ T Cells," Nature 327:710–713 (1987).
Smith, D. H. et al., "Blocking of HIV–1 Infectivity by a Soluble, Secreted Form of the CD4 Antigen," Science 238:1704–1707 (1987).
Estess, P. et al., "Analysis of T–Cell Receptor Structure and Function Using Chimeric T–Cell Receptor/Immunoglobulin Molecules," J. Cell. Biochem. (Suppl. 11D):Abstract 331, p. 258 (1987).
Clark, S. et al., "Peptide and nucleotide sequences of rat CD4 (W3/25) antigen: Evidence for derivation from a structure with four immuno–globulin–related domains," Proc. Natl. Acad. Sci. (USA) 84:1649 (1987).
Palker, T. J. et al., "A Conserved Region at the COOH Terminus of Human Immunodeficiency Virus gp120 Envelope Protein Contains an Immunodominant Epitope," Proc. Natl. Acad. Sci. (USA) 84:2479–2483 (1987).
Neuberger, M. S. et al., "Recombinant Antibodies Possessing Novel Effector Functions," Nature 312:604–608 (1984).

(List continued on next page.)

Primary Examiner—John Ulm
Attorney, Agent, or Firm—Greenlee, Winner and Sullivan, PC

[57] ABSTRACT

The invention relates to a fusion protein which comprises an immunoglobulin of the IgM, IgG1 or IgG3 immunoglobulin class, wherein the variable region of the light or heavy chain has been replaced with CD4 or fragment thereof which is capable of binding to gp120. The invention also relates to an immunoglobulin-like molecule comprising the fusion protein of the invention together with an immunoglobulin light or heavy chain. The invention also relates to a method of treating HIV or SIV infection comprising administering the fusion proteins or immunoglobulin-like molecules of the invention to an animal. The invention also relates to assays for HIV or SIV comprising contacting a sample suspected of containing HIV or SIV gp120 with the immunoglobulin-like molecule or fusion protein of the invention, and detecting whether a complex is formed.

14 Claims, No Drawings

OTHER PUBLICATIONS

Rusche, J. A. et al., "Antibodies that Inhibit Fusion of Human Immuno–deficiency Virus–Infected Cells Bind a 24–Amino Acid Sequence of the Viral Envelope, gp120," Proc. Natl. Acad. Sci. (USA) 85:3198–3202 (1988).

Boulianne, G. L. et al., "Production of Functional Chimaeric Mouse/Human Antibody," Nature 312:643–646 (1984).

The International Search Report for corresponding International Application No. PCT/US89/00238.

NUCLEIC ACID ENCODING IG-CD4 FUSION PROTEINS

CROSS-REFERENCE TO RELATED APPLICATION

This application is a continuation of application Ser. No. 08/057,952, filed Apr. 12, 1993, now abandoned, which is a continuation application of Ser. No. 07/896,781, filed Jun. 9, 1992, now abandoned, which is a continuation of application Ser. No. 07/299,596, filed Jan. 23, 1989, now abandoned, which is a continuation-in-part of application Ser. No. 07/147,351, filed Jan. 22, 1988, now abandoned.

FIELD OF THE INVENTION

The invention is in the field of recombinant genetics.

BACKGROUND OF THE INVENTION

The human and simian immunodeficiency viruses HIV and SIV are the causative agents of Acquired Immune Deficiency Syndrome (AIDS) and Simian Immunodeficiency Syndrome (SIDS), respectively. See Curren, J. et al., *Science* 329:1359–1357 (1985); Weiss, R. et al., *Nature* 324:572–575 (1986). The HIV virus contains an envelope glycoprotein, gp120 which binds to the CD4 protein present on the surface of helper T lymphocytes, macrophages and other cells. Dalgleish et al. *Nature,* 312:763 (1984). After the gp120 binds to CD4, virus entry is facilitated by an envelope-mediated fusion of the viral target cell membranes.

During the course of infection, the host organism develops antibodies against viral proteins, including the major envelope glycoproteins gp120 and gp41. Despite this humoral immunity, the disease progresses, resulting in a lethal immunosuppression characterized by multiple opportunistic infections, parasitemia, dementia and death. The failure of host anti-viral antibodies to arrest the progression of the disease represents one of the most vexing and alarming aspects of the infection, and augurs poorly for vaccination efforts based upon conventional approaches.

Two factors may play a role in the inefficacy of the humoral response to immunodeficiency viruses. First, like other RNA viruses (and like retroviruses in particular), the immunodeficiency viruses show a high mutation rate which allows antigenic variation to progress at a high rate in response to host immune surveillance. Second, the envelope glycoproteins themselves are heavily glycosylated molecules presenting few epitopes suitable for high affinity antibody binding. The poorly antigenic, "moving" target which the viral envelope presents, allows the host little opportunity for restricting viral infection by specific antibody production.

Cells infected by HIV express the gp120 glycoprotein on their surface. Gp120 mediates fusion events among $CD4^+$ cells via a reaction similar to that by which the virus enters the uninfected cell, leading to the formation of short-lived multinucleated giant cells. Syncytium formation is dependent on a direct interaction of the gp120 envelope glycoprotein with the CD4 protein. Dalgleish et al., supra, Klatzmann, D. et al., *Nature* 312:763 (1984); McDougal, J. S. et al. *Science,* 231:382 (1986); Sodroski, J. et al., *Nature,* 322:470 (1986); Lifson, J. D. et al., *Nature,* 323:725 (1986); Sodroski, J. et al., *Nature,* 321:412 (1986).

The CD4 protein consists of a 370 amino acid extracellular region containing four immunoglobulin-like domains, a membrane spanning domain, and a charged intracellular region of 40 amino acid residues. Maddon, P. et al., *Cell* 42:93 (1985); Clark, S. et al., *Proc. Natl. Acad. Sci.* (USA) 84:1649 (1987).

Evidence that CD4-gp120 binding is responsible for viral infection of cells bearing the CD4 antigen includes the finding that a specific complex is formed between gp120 and CD4. McDougal et al., supra. Other workers have shown that cell lines, which were non-infective for HIV, were converted to infectable cell lines following transfection and expression of the human CD4 cDNA gene. Maddon et al., *Cell* 47:333–348 (1986).

In contrast to the majority of antibody-envelope interactions, the receptor-envelope interaction is characterized by a high affinity ($K_a \approx 10^8$ l/mole) immutable association. Moreover, the affinity of the virus for CD4 is at least 3 orders of magnitude higher than the affinity of CD4 for its putative endogenous ligand, the MHC class II antigens. Indeed, to date, a specific physical association between monomeric CD4 and class II antigens has not been demonstrated.

In response to bacterial or other particle infection, the host organism usually produces serum antibodies that bind to specific proteins or carbohydrates on the bacterial or particle surface, coating the bacteria. This antibody coat on the bacterium or other particle stimulates cytolysis by Fc-receptor-bearing lymphoid cells by antibody-dependent cellular toxicity (ADCC). Other serum proteins, collectively called complement (C), bind to antibody-coated targets, and also can coat foreign particles nonspecifically. They cause cell death by lysis, or stimulate ingestion by binding to specific receptors on the macrophage called complement receptors. See Darnell J. et al., in *Molecular Cell Biology,* Scientific American Books, pp. 641 and 1087 (1986).

The most effective complement activating classes of human Ig are IgM and IgG1. The complement system consists of 14 proteins that, acting in order, cause lysis of cells. Nearly all of the C proteins exist in normal serum as inactive precursors. When activated, some become highly specific proteolytic enzymes whose substrate is the next protein in a sequential chain reaction.

The entire C sequence can be triggered by either of two initiation pathways. In one (the classic pathway), Ab—Ag complexes bind and activate C1, C4 and C2 to form a C3-splitting enzyme. In the second pathway, polysaccharides commonly on the surface of many bacteria and fungi bind with trace amounts of a C3 fragment and then with two other proteins (factor B and properdin) to form another C3-splitting enzyme. Once C3 is split by either pathway, the way is open for the remaining sequence of steps which lead to cell lysis. See Davis, B. D., et al., In *Microbiology,* 3rd ed., Harper and Row, Philadelphia, Pa., pp. 452–466 (1980).

A number of workers have disclosed methods for preparing hybrid proteins. For example, Murphy, U.S. Pat. No. 4,675,382 (1987), discloses the use of recombinant DNA techniques to make hybrid protein molecules by forming the desired fused gene coding for a hybrid protein of diptheria toxin and a polypeptide ligand such as a hormone, followed by expression of the fused gene.

Many workers have prepared monoclonal antibodies (Mabs) by recombinant DNA techniques. Monoclonal antibodies are highly specific well-characterized molecules in both primary and tertiary structure. They have been widely used for in vitro immunochemical characterization and quantitation of antigens. Genes for heavy and light chains have been introduced into appropriate hosts and expressed, followed by reaggregation of the individual chains into functional antibody molecules (see, for example, Munro, Nature 312:597 (1984); Morrison, S. L., Science 229:1202 (1985); Oi et al., Biotechniques 4:214 (1986); Wood et al., Nature 314:446–449 (1985)). Light- and heavy-chain variable regions have been cloned and expressed in foreign hosts wherein they maintained their binding ability (Moore et al., European Patent Application 0088994 (published Sep. 21, 1983)).

Chimeric or hybrid antibodies have also been prepared by recombinant DNA techniques. Oi and Morrison, Biotechniques 4:214 (1986) describe a strategy for producing such chimeric antibodies which include a chimeric human IgG anti-leu3 antibody.

Gascoigne, N. R. J., et al., Proc. Natl. Acad. Sci. (USA) 84:2936–2940 (1987) disclose the preparation of a chimeric gene construct containing a T-cell receptor α-chain variable (V) domain and the constant (C) region coding sequence of an immunoglobulin γ2a molecule. Cells transfected with the chimeric gene synthesize a protein product that expresses immunoglobulin and T-cell receptor antigenic determinants as well as protein A binding sites. This protein associates with a normal λ chain to form an apparently normal tetrameric ($H_2L_2$, where H=heavy and L=light) immunoglobulin molecule that is secreted.

Sharon, J., et al., Nature 309:54 (1984), disclose construction of a chimeric gene encoding the variable (V) region of a mouse heavy chain specific for the hapten azophenylarsonate and the constant (C) region of a mouse kappa light chain ($V_HC_K$). This gene was introduced into a mouse myeloma cell line. The chimeric gene was expressed to give a protein which associated with light chains secreted from the myeloma cell line to give an antibody molecule specific for azophenylarsonate.

Morrison, Science 229:1202 (1985), discloses that variable light- or variable heavy-chain regions can be attached to a non-Ig sequence to create fusion proteins. This article states that the potential uses for the fusion proteins are three: (1) to attach antibody specifically to enzymes for use in assays; (2) to isolate non-Ig proteins by antigen columns; and (3) to specifically deliver toxic agents.

Recent techniques for the stable introduction of immunoglobulin genes into myeloma cells (Banerji, J., et al., Cell 33:729–740 (1983); Potter, H., et al., Proc. Natl. Acad. Sci. (USA) 81:7161–7165 (1984)), coupled with detailed structural information, have permitted the use of in vitro DNA methods such as mutagenesis, to generate recombinant antibodies possessing novel properties.

PCT Application WO87/02671 discloses methods for producing genetically engineered antibodies of desired variable region specificity and constant region properties through gene cloning and expression of light and heavy chains. The mRNA from cloned hybridoma B cell lines which produce monoclonal antibodies of desired specificity is isolated for cDNA cloning. The generation of light and heavy chain coding sequences is accomplished by excising the cloned variable regions and ligating them to light or heavy chain module vectors. This gives cDNA sequences which code for immunoglobulin chains. The lack of introns allows these cDNA sequences to be expressed in prokaryotic hosts, such as bacteria, or in lower eukaryotic hosts, such as yeast.

The generation of chimeric antibodies in which the antigen-binding portion of the immunoglobulin is fused to other moieties has been demonstrated. Examples of non-immunoglobulin genes fused to antibodies include Staphylococcus aureus nuclease, the mouse oncogene c-myc, and the Klenow fragment of E. coli DNA polymerase I (Neuberger, M. S., et al., Nature 312:604–612 (1984); Neuberger, M. S., Trends in Biochemical Science, 347–349 (1985)). European Patent Application 120,694 discloses the genetic engineering of the variable and constant regions of an immunoglobulin molecule that is expressed in E. coli host cells. It is further disclosed that the immunoglobulin molecule may be synthesized by a host cell with another peptide moiety attached to one of the constant domains. Such peptide moieties are described as either cytotoxic or enzymatic. The application and the examples describe the use of a lambda-like chain derived from a monoclonal antibody which binds to 4-hydroxy-3-nitrophenyl (NP) haptens.

European Patent Application 125,023 relates to the use of recombinant DNA techniques to produce immunoglobulin molecules that are chimeric or otherwise modified. One of the uses described for these immunoglobulin molecules is for whole-body diagnosis and treatment by injection of the antibodies directed to specific target tissues. The presence of the disease can be determined by attaching a suitable label to the antibodies, or the diseased tissue can be attacked by carrying a suitable drug with the antibodies. The application describes antibodies engineered to aid the specific delivery of an agent as "altered antibodies."PCT Application WO83/101533 describes chimeric antibodies wherein the variable region of an immunoglobulin molecule is linked to a portion of a second protein which may comprise the active portion of an enzyme.

Boulianne et al., Nature 32:643 (1984) constructed an immunoglobulin gene in which the DNA segments that encode mouse variable regions specific for the hapten trinitrophenol (TNP) are joined to segments that encode human mu and kappa regions. These chimeric genes were expressed to give functional TNP-binding chimeric IgM.

Morrison et al., P.N.A.S. (USA) 81:6851 (1984), disclose a chimeric molecule utilizing the heavy-chain variable region exons of an anti-phosphoryl choline myeloma protein G, which were joined to the exons of either human kappa light-chain gene. The genes were transfected into mouse myeloma cell lines, generating transformed cells that produced chimeric mouse-human IgG with antigen-binding function.

Despite the progress that has been achieved on determining the mechanism of HIV infection, a need continues to exist for methods of treating HIV infections.

SUMMARY OF THE INVENTION

The invention relates to a gene comprising a DNA sequence which encodes a fusion protein comprising 1) CD4, or a fragment thereof which binds to HIV gp120, and 2) an immunoglobulin light or heavy chain; wherein said CD4 or HIV gp120-binding fragment thereof replaces the variable region of the light or heavy immunoglobulin chain.

The invention also relates to vectors containing the gene of the invention and hosts transformed with the vectors.

The invention also relates to a method of producing a fusion protein comprising CD4, or fragment thereof which binds to HIV gp120, and an immunoglobulin light or heavy chain, wherein the variable region of the immunoglobulin light or heavy chain has been substituted with CD4, or HIV gp120-binding fragment thereof, which comprises:

cultivating in a nutrient medium under protein producing conditions, a host strain transformed with the vector containing the gene of the invention, said vector further comprising expression signals which are recognized by said host strain and direct expression of said fusion protein, and recovering the fusion protein so produced.

The invention also relates to a fusion protein comprising CD4, or fragment thereof which is capable of binding to HIV gp120, fused at the C-terminus to a second protein which comprises an immunoglobulin light or heavy chain, wherein the variable region of said light or heavy chain is substituted with CD4 or a HIV gp120 binding fragment thereof.

The invention also relates to an immunoglobulin-like molecule comprising the fusion protein of the invention together with an immunoglobulin light or heavy-chain, wherein said immunoglobulin like molecule binds HIV gp120.

The IgG1 fusion proteins and immunoglobulin-like molecules may be useful for both complement-mediated and cell-mediated (ADCC) immunity, while the IgM fusion proteins are useful principally through complement-mediated immunity.

The invention also relates to a complex between the fusion proteins and immunoglobulin-like molecule of the invention and HIV gp120.

The invention also relates to a method for treating HIV or SIV infections comprising administering the fusion protein or immunoglobulin-like molecule of the invention to an animal.

The invention further relates to a method for detecting HIV gp120 in a sample comprising contacting a sample suspected of containing HIV or gp120 with the fusion protein or immunoglobulin-like molecule of the invention, and detecting whether a complex has formed.

DESCRIPTION OF THE PREFERRED EMBODIMENTS

The invention is directed to a protein gene which comprises
1) a DNA sequence which codes for CD4, or fragment thereof which binds to HIV gp120, fused to
2) a DNA sequence which encodes an immunoglobulin heavy chain.

Preferably, the antibody has effector function.

The invention is also directed to a protein gene which comprises
1) a DNA sequence which codes for CD4, or fragment thereof which binds to HIV gp120, fused to
2) a DNA sequence which encodes an immunoglobulin light chain; wherein said sequence which codes for CD4, or HIV gp120-binding fragment thereof, replaces the variable region of the light immunoglobulin chain.

The invention is also directed to the expression of these novel fusion proteins in transformed hosts and the use thereof to treat and diagnose HIV infections. In particular, the invention relates to expressing said genes in mammalian hosts which express complementary light or heavy chain immunoglobulins to give immunoglobulin-like molecules which have antibody effector function and also bind to HIV or SIV gp120.

The term "antibody effector function" as used herein denotes the ability to fix complement or to activate ADCC.

The fusion proteins and immunoglobulin-like molecules may be administered to an animal for the purpose of treating HIV or SIV infections. By the term "HIV infections" is intended the condition of having AIDS, AIDS related complex (ARC) or where an animal harbors the AIDS virus but does not exhibit the clinical symptoms of AIDS or ARC. By the term "SIV infections" is intended the condition of being infected with simian immunodeficiency virus.

By the term "animal" is intended all animals which may derive benefit from the administration of fusion proteins and immunoglobulin-like molecules of the invention. Foremost among such animals are humans; however, the invention is not intended to be so limited.

By the term "fusion protein" is intended a fused protein comprising CD4, or fragment thereof which is capable of binding to gp120, linked at its C-terminus to an immunoglobulin chain wherein a portion of the N-terminus of the immunoglobulin is replaced with CD4. In general, that portion of immunoglobulin which is deleted is the variable region. The fusion proteins of the invention may also comprise immunoglobulins where more than Just the variable region has been deleted and replaced with CD4 or HIV gp120 binding fragment thereof. For example, the $V_H$ and CH1 regions of an immunoglobulin chain may be deleted. Preferably, any amount of the N-terminus of the immunoglobulin heavy chain can be deleted as long as the remaining fragment has antibody effector function. The minimum sequence required for binding complement encompasses domains CH2 and CH3. Joining of Fc portions by the hinge region is advantageous for increasing the efficiency of complement binding.

The CD4 portion of the fusion protein may comprise the complete CD4 sequence, the 370 amino acid extracellular region and the membrane spanning domain, or the extracellular region. The fusion protein may comprise fragments of the extracellular region obtained by cutting the DNA sequence which encodes CD4.

The fusion proteins and immunoglobulin-like molecules may be administered to an animal for the purpose of treating HIV or SIV infections. By the term "HIV infections" is intended the condition of having AIDS, AIDS related complex (ARC) or where an animal harbors the AIDS virus but does not exhibit the clinical symptoms of AIDS or ARC. By the term "SIV infections" is intended the condition of being infected with simian immunodeficiency virus.

By the term "animal" is intended all animals which may derive benefit from the administration of fusion proteins and immunoglobulin-like molecules of the invention. Foremost among such animals are humans; however, the invention is not intended to be so limited.

Where the fusion protein comprises an immunoglobulin light chain, it is necessary that no more of the Ig chain be deleted than is necessary to form a stable complex with a heavy chain Ig. In particular, the cysteine residues necessary for disulfide bond formation must be preserved on both the heavy and light chain moieties.

When expressed in a host, e.g., a mammalian cell, the fusion protein may associate with other light or heavy Ig chains secreted by the cell to give a functioning immunoglobulin-like molecule which is capable of binding to gp120. The gp120 may be in solution, expressed on the surface of infected cells, or may be present on the surface of the HIV virus itself. Alternatively, the fusion protein may be expressed in a mammalian cell which does not secrete other light or heavy Ig chains. When expressed under these conditions, the fusion protein may form a homodimer.

Genomic or CDNA sequences may be used in the practice of the invention. Genomic sequences are expressed efficiently in myeloma cells, since they contain native promoter structures.

The constant regions of the antibody cloned and used in the chimeric immunoglobulin-like molecule may be derived from any mammalian source. The constant regions may be complement binding or ADCC active. However, preliminary work (see Examples) indicates that the fusion proteins of the invention may mediate HIV or SIV infected cell death by an ADCC or complement-independent mechanism. The constant regions may be derived from any appropriate isotype, including IgG1, IgG3, or IgM.

The joining of various DNA fragments, is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligases. The genetic construct may optionally encode a leader sequence to allow efficient expression of the fusion protein. For example, the leader sequence utilized by Maddon et al., *Cell* 42:93–104 (1985) for the expression of CD4 may be used.

For cDNA, the cDNA may be cloned and the resulting clone screened, for example, by use of a complementary probe or by assay for expressed CD4 using an antibody as disclosed by Dalgleish et al., *Nature* 312:763–766 (1984); Klatzmann et al., *Immunol. Today* 7:291–297 (1986); McDougal et al., *J. Immunol.* 135:3151–3162 (1985); and McDougal, J. et al., *J. Immunol,* 137:2937–2944 (1986).

To express the fusion hybrid protein, transcriptional and translational signals recognized by an appropriate host element are necessary. Eukaryotic hosts which may be used include mammalian cells capable of culture in vitro, particularly leukocytes, more particularly myeloma cells or other transformed or oncogenic lymphocytes, e.g., EBV-transformed cells. Alternatively, non-mammalian cells may be employed, such as bacteria, fungi, e.g., yeast, filamentous fungi, or the like.

Preferred hosts for fusion protein production are mammalian cells, grown in vitro in tissue culture or in vivo in animals. Mammalian cells provide post translational modification to immunoglobulin protein molecules which provide for correct folding and glycosylation of appropriate sites. Mammalian cells which may be useful as hosts include cells of fibroblast origins such as VERO or CHO-K1 or cells of lymphoid origin, such as the hybridoma SP2/0-AG14 or the myeloma P3x63Sgh, and their derivatives. For the purpose of preparing an immunoglobulin-like molecule, a plasmid containing a gene which encodes a heavy chain immunoglobulin, wherein the variable region has been replaced with CD4 or fragment thereof which binds to gp120, may be introduced, for example, into J558L myeloma cells, a mouse plasmacytoma expressing the lambda-1 light chain but which does not express a heavy chain (see Oi et al., *P.N.A.S.* (USA) 80:825–829 (1983)). Other preferred hosts include COS cells, BHK cells and hepatoma cells.

The constructs may be Joined together to form a single DNA segment or may be maintained as separate segments, by themselves or in conjunction with vectors.

Where the fusion protein is not glycosylated, any host may be used to express the protein which is compatible with replicon and control sequences in the expression plasmid. In general, vectors containing replicon and control sequences are derived from species compatible with a host cell are used in connection with the host. The vector ordinarily carries a replicon site, as well as specific genes which are capable of providing phenotypic selection in transformed cells. The expression of the fusion protein can also be placed under control with other regulatory sequences which may be homologous to the organism in its untransformed state. For example, lactose-dependent *E. coli* chromosomal DNA comprises a lactose or lac operon which mediates lactose utilization by elaborating the enzyme beta-galactosidase. The lac control elements may be obtained from bacterial phage lambda plac5, which is infective for *E. coli*. The lac promoter-operator system can be induced by IPTG.

Other promoters/operator systems or portions thereof can be employed as well. For example, colicin E1, galactose, alkaline phosphatase, tryptophan, xylose, tax, and the like can be used.

For mammalian hosts, several possible vector systems are available for expression. One class of vectors utilize DNA elements which are derived from animal viruses such as bovine papilloma virus, polyoma virus, adenovirus, vaccinia virus, baculovirus, retroviruses (RSV, MMTV or MOMLV), or SV40 virus. Cells which have stably integrated the DNA into their chromosomes may be selected by introducing one or more markers which allow selection of transfected host cells. The marker may provide for prototropy to an auxotrophic host, biocide resistance, e.g., antibiotics, or heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements includes those described by Okayama, H., *Mol. Cel. Biol.,* 1:280 (1983) and others.

Once the vector or DNA sequence containing the constructs has been prepared for expression, the DNA constructs may be introduced to an appropriate host. Various techniques may be employed, such as protoplast fusion, calcium phosphate precipitation, electroporation or other conventional techniques. After the fusion, the cells are grown in media and screened for the appropriate activity. Expression of the gene(s) results in production of the fusion protein. This expressed fusion protein may then be subject to further assembly to form the immunoglobulin-like molecule.

The host cells for immunoglobulin production may be immortalized cells, primarily myeloma or lymphoma cells. These cells may be grown in appropriate nutrient medium in culture flasks or injected into a synergistic host, e.g., mouse or a rat, or immunodeficient host or host site, e.g., nude mouse or hamster pouch. In particular, the cells may be introduced into the abdominal cavity of an animal to allow production of ascites fluid which contains the immunoglobulin-like molecule. Alternatively, the cells may be injected subcutaneously and the chimeric antibody is harvested from the blood of the host. The cells may be used in the same manner as hybridoma cells. See Diamond et al., *N. Eng. J. Med.* 304:1344 (1981), and Kennatt, McKearn and Bechtol (Eds.), *Monoclonal Antibodies: Hybridomas:—A New Dimension in Biologic Analysis,* Plenum, 1980.

The fusion proteins and immunoglobulin-like molecules of the invention may be isolated and purified in accordance with conventional conditions, such as extraction, precipitation, chromatography, affinity chromatography, electrophoresis or the like. For example, the IgG1 fusion proteins may be purified by passing a solution through a column which contains immobilized protein A or protein G which selectively binds the Fc portion of the fusion protein. See, for example, Reis, K. J., et al., *J. Immunol.* 132:3098–3102 (1984); PCT Application, Publication No. WO87/00329. The chimeric antibody may the be eluted by treatment with a chaotropic salt or by elution with aqueous acetic acid (1 M).

Alternatively the fusion proteins may be purified on anti-CD4 antibody columns, or on anti-immunoglobulin antibody columns.

In one embodiment of the invention, cDNA sequences which encode CD4, or a fragment thereof which binds gp120, may be ligated into an expression plasmid which codes for an antibody wherein the variable region of the gene has been deleted. Methods for the preparation of genes which encode the heavy or light chain constant regions of immunoglobulins are taught, for example, by Robinson, R. et al., PCT Application, Publication No. WO87-02671.

Preferred immunoglobulin-like molecules which contain CD4, or fragments thereof, contain the constant region of an IgM, IgG1 or IgG3 antibody which binds complement at the Fc region.

The fusion protein and immunoglobulin-like molecules of the invention may be used for the treatment of HIV viral infections. The fusion protein complexes to gp120 which is expressed on infected cells. Although the inventor is not bound by a particular theory, it appears that the Fc portion of the hybrid fusion protein may bind with complement, which mediates destruction of the cell. In this manner, infected cells are destroyed so that additional viral particle production is stopped.

For the purpose of treating HIV infections, the fusion protein or immunoglobulin-like molecule of the invention may additionally contain a radiolabel or therapeutic agent which enhances destruction of the HIV particle or HIV-infected cell.

Examples of radioisotopes which can be bound to the fusion protein or immunoglobulin-like molecule of the invention for use in HIV therapy are $^{125}I$, $^{131}I$, $^{90}Y$, $^{67}Cu$, $^{217}Bi$, $^{211}At$, $^{212}Pb$, $^{47}Sc$, and $^{109}Pd$. Optionally, a label such as boron can be used which emits $\alpha$ and $\beta$ particles upon bombardment with neutron radiation.

For in vivo diagnosis radionucleotides may be bound to the fusion protein or immunoglobulin-like molecule of the invention either directly or by using an intermediary functional group. An intermediary group which is often used to bind radioisotopes, which exist as metallic cations, to antibodies is diethylenetriaminepentaacetic acid (DTPA). Typical examples of metallic cations which are bound in this manner are $^{99m}Tc$ $^{123}I$, $^{111}In$, $^{131}I$, $^{97}Ru$, $^{67}Cu$, $^{67}Ga$, and $^{68}Ga$.

Moreover, the fusion protein and immunoglobulin-like molecule of the invention may be tagged with an NMR imaging agent which include paramagnetic atoms. The use of an NMR imaging agent allows the in vivo diagnosis of the presence of and the extent of HIV infection within a patient using NMR techniques. Elements which are particularly useful in this manner are $^{157}Gd$, $^{55}Mn$, $^{162}Dy$, $^{52}Cr$, and $^{56}Fe$.

Therapeutic agents may include, for example, bacterial toxins such as diphtheria toxin, or ricin. Methods for producing fusion proteins comprising fragment A of diphtheria toxin are taught in U.S. Pat. No. 4,675,382 (1987). Diphtheria toxin contains two polypeptide chains. The B chain binds the toxin to a receptor on a cell surface. The A chain actually enters the cytoplasm and inhibits protein synthesis by inactivating elongation factor 2, the factor that translocates ribosomes along mRNA concomitant with hydrolysis of ETP. See Darnell, J. et al., in *Molecular Cell Biology,* Scientific American Books, Inc., page 662 (1986). Alternatively, a fusion protein comprising ricin, a toxic lectin, may be prepared.

Introduction of the chimeric molecules by gene therapy may also be contemplated, for example, using retroviruses or other means to introduce the genetic material encoding the fusion proteins into suitable target tissues. In this embodiment, the target tissues having the cloned genes of the invention may then produce the fusion protein in vivo.

The dose ranges for the administration of the fusion protein or immunoglobulin-like molecule of the invention are those which are large enough to produce the desired effect whereby the symptoms of HIV or SIV infection are ameliorated. The dosage should not be so large as to cause adverse side effects, such as unwanted cross-reactions, anaphylactic reactions, and the like. Generally, the dosage will vary with the age, condition, sex and extent of disease in the patient, counterindications, if any, immune tolerance and other such variables, to be adjusted by the individual physician. Dosage can vary from 0.01 mg/kg to 50 mg/kg, preferably 0.1 mg/kg to 1.0 mg/kg, of the immunoglobulin-like molecule in one or more administrations daily, for one or several days. The immunoglobulin-like molecule can be administered parenterally by injection or by gradual perfusion over time. They can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, poly-ethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, antioxidants, chelating agents, inert gases and the like. See, generally, *Remington's Pharmaceutical Science,* 16th Ed., Mack Eds., 1980.

The invention also relates to a method for preparing a medicament or pharmaceutical composition comprising the components of the invention, the medicament being used for therapy of HIV or SIV infection in animals.

The detection and quantitation of antigenic substances and biological samples frequently utilized immunoassay techniques. These techniques are based upon the formation of the complex between the antigenic substance, e.g., gp120, being assayed and an antibody or antibodies in which one or the other member of the complex may be detectably labeled. In the present invention, the immunoglobulin-like molecule or fusion protein may be labeled with any conventional label.

Thus, the hybrid fusion protein or immunoglobulin-like molecule of the invention can also be used in assay for HIV or SIV viral infection in a biological sample by contacting a sample, derived from an animal suspected of having an HIV or SIV infection, with the fusion protein or immunoglobulin-like molecule of the invention, and detecting whether a complex with gp120, either alone or on the surface of an HIV-infected cell, has formed.

For example, a biological sample may be treated with nitrocellulose, or other solid support which is capable of immobilizing cells, cell particles or soluble protein. The support may then be washed with suitable buffers followed by treatment with the fusion protein which may be detectably labeled. The solid phase support may then be washed with the buffer a second time to remove unbound fusion protein and the label on the fusion protein detected.

In carrying out the assay of the present invention on a sample containing gp120, the process comprises:

a) contacting a sample suspected containing gp120 with a solid support to effect immobilization of gp120, or cell which expresses gp120 on its surface;

b) contacting said solid support with the detectably labeled immunoglobulin-like molecule or fusion protein of the invention;

c) incubating said detectably labeled immunoglobulin-like molecule with said support for a sufficient amount of time to allow the immunoglobulin-like molecule or fusion protein to bind to the immobilized gp120 or cell which expresses gp120 on its surface;

d) separating the solid phase support from the incubation mixture obtained in step c); and e) detecting the bound immunoglobulin-like molecule or fusion protein and thereby detecting and quantifying gp120.

Alternatively, labeled immunoglobulin-like molecule (or fusion protein) -gp120 complex in a sample may be separated from a reaction mixture by contacting the complex with an immobilized antibody or protein which is specific for an immunoglobulin or, e.g., protein A, protein G, anti-IgM or anti-IgG antibodies. Such anti-immunoglobulin antibodies may be monoclonal or polyclonal. The solid support may then be washed with suitable buffers to give an immobilized gp120-labeled immunoglobulin-like molecule antibody complex. The label on the fusion protein may then be detected to give a measure of endogenous gp120 and, thereby, the presence of HIV.

This aspect of the invention relates to a method for detecting HIV or SIV viral infection in a sample comprising (a) contacting a sample suspected of containing gp120 with a fusion protein or immunoglobulin-like molecule comprising CD4, or fragment thereof which binds to gp120, and the Fc portion of an immunoglobulin chain, (b) detecting whether a complex is formed.

The invention also relates to a method of detecting gp120 in a sample, further comprising (c) contacting the mixture obtained in step (a) with an Fc binding molecule, such as an antibody, protein A, or protein G, which is immobilized on a solid phase support and is specific for the hybrid fusion protein, to give a gp120 fusion protein-immobilized antibody complex (d) washing the solid phase support obtained in step (c) to remove unbound fusion protein, (e) and detecting the label on the hybrid fusion protein.

Of course, the specific concentrations of detectably labeled immunoglobulin-like molecule (or fusion protein) and gp120, the temperature and time of incubation, as well as other assay conditions may be varied, depending on various factors including the concentration of gp120 in the sample, the nature of the sample, and the like. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the immunoglobulin-like molecule or fusion protein of the present invention can be detectably labeled is by linking the same to an enzyme. This enzyme, in turn, when later exposed to its substrate, will react with the substrate in such a manner as to produce a chemical moiety which can be detected as, for example, by spectrophotometric, fluorometric or by visual means. Enzymes which can be used to detectably label the immunoglobulin-like molecule or fusion protein of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The immunoglobulin-like molecule or fusion protein of the present invention may also be labeled with a radioactive isotope which can be determined by such means as the use of a gamma counter or a scintillation counter or by autoradiography. Isotopes which are particularly useful for the purpose of the present invention are: $^{3}H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$ and $^{75}Se$.

It is also possible to label the immunoglobulin-like molecule or fusion protein with a fluorescent compound. When the fluorescently labeled immunoglobulin-like molecule is exposed to light of the proper wave length, its presence can then be detected due to the fluorescence of the dye. Among the most commonly used fluorescent labelling compounds are fluorescein isothiocyanate, rhodamine, phycoerytherin, phycocyanin, allophycocyanin, o-phthaldehyde and fluorescamine.

The immunoglobulin-like molecule or fusion protein of the invention can also be detectably labeled using fluorescence emitting metals such as $^{152}Eu$, or others of the lanthanide series. These metals can be attached to the immunoglobulin-like molecule or fusion protein using such metal chelating groups as diethylenetriaminepentaacetic acid (DTPA) or ethylenediaminetetraacetic acid (EDTA).

The immunoglobulin-like molecule or fusion protein of the present invention also can be detectably labeled by coupling it to a chemiluminescent compound. The presence of the chemiluminescent-tagged immunoglobulin-like molecule or fusion protein is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the immunoglobulin-like molecule or fusion protein of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the immunoglobulin-like molecule or fusion protein may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

The assay of the present invention is ideally suited for the preparation of a kit. Such a kit may comprise a carrier means being compartmentalized to receive in close confinement therewith one or more container means such as vials, tubes and the like, each of said container means comprising the separate elements of the immunoassay. For example, there may be a container means containing a solid phase support, and further container means containing the detectably labeled immunoglobulin-like molecule or fusion protein in solution. Further container means may contain standard solutions comprising serial dilutions of analytes such as gp120 or fragments thereof to be detected. The standard solutions of these analytes may be used to prepare a standard curve with the concentration of gp120 plotted on the abscissa and the detection signal on the ordinate. The results obtained from a sample containing gp120 may be interpolated from such a plot to give the concentration of gp120.

The immunoglobulin-like molecule or fusion protein of the present invention can also be used as a stain for tissue sections. For example, a labeled immunoglobulin-like molecule comprising CD4 or fragment thereof which binds to gp120 may be contacted with a tissue section, e.g., a brain biopsy specimen. This section may then be washed and the label detected.

The following examples are illustrative, but not limiting the method and composition of the present invention. Other suitable modifications and adaptations which are obvious to this skill in the art are within the spirit and scope of this invention.

EXAMPLES

Example 1
Preparation of CD4-Ig cDNA Constructs

The extracellular portion of the CD4 molecule (See Madden, P. J., et al., Cell 42:93–104 (1985)) was fused at three locations in a human IgG1 heavy chain constant region gene by means of a synthetic splice donor linker molecule. To exploit the splice donor linker, a BamHI linker having the sequence CGCGGATCCGCG was first inserted at amino acid residue 395 of the CD4 precursor sequence (nucleotide residue 1295). A synthetic splice donor sequence

GATCCCGAGGGTGAGTACTA

GGCTCCCACTCATGATTCGA bounded by BamHI and HindIII complementary ends was created and fused to the HindIII site in the intron preceding the CH1 domain, to the EspI site in the intron preceding the hinge domain, and to the BanI site preceding the CH2 domain of the IgG1 genomic sequence. Assembly of the chimeric genes by ligation at the BamHI site afforded molecules in which either the variable (V) region, the V+CH1 regions, or the V, CH1 and hinge regions were replaced by CD4. In the last case, the chimeric molecule is expected to form a monomer structure, while in the former, a dimeric molecule is expected.

One such genetic construct which contains the DNA sequence which encodes CD4 linked to human IgG1 at the Hind3 site upstream of the CH1 region (fusion protein CD4H-1) is depicted in Table 1. The plasmid containing this genetic construct (pCD4Hγ1) has been deposited in E. coli (MC1061/P3) at the American Type Culture Collection (ATCC) under the terms of the Budapest Treaty and given accession number 67611.

A second genetic construct which contains the DNA sequence which encodes CD4 linked to human IgG1 at the Esp site upstream of the hinge region (fusion protein CD4Eγ1) is depicted in Table 2. The plasmid containing this genetic construct (pCD4Eγ1) has been deposited in E. coli (MC1061/P3) at the ATCC under the terms of the Budapest Treaty and given accession number 67610.

A third genetic construct which contains the DNA sequence which encodes CD4 linked to human IgM at the Mst2 site upstream of the CH1 region (fusion protein CD4Mg) is depicted in Table 3. The plasmid containing this genetic construct (pCD4Mµ) has been deposited in E. coli (MC1061/P3) at the ATCC under the terms of the Budapest Treaty and given accession number 67609.

A fourth genetic construct which contains the DNA sequence which encodes CD4 linked to human IgM at the Pst site upstream of the CH2 region (fusion protein CD4Pµ) is depicted in Table 4. The plasmid containing this genetic construct (pCD4Pµ) has been deposited in E. coli (MC1061/P3) at the ATCC under the terms of the Budapest Treaty and given accession number 67608.

A fifth genetic construct which contains the DNA sequence which encodes CD4 linked to human IgG1 at the Ban1 site downstream from the hinge region (fusion protein CD4Bγ1) is depicted in Table 5.

Two similar constructs were prepared from the human IgM heavy chain constant region by fusion with the introns upstream of the µ CH1 and CH2 domains at an MstII site and a PstI site respectively. The fusions were made by joining the PstI site of the CD4/IgG1 construct fused at the Esp site in IgG1 gene to the MstII and Pst sites in the IgM gene. In the first instance, this was performed by treatment of the Pst end with T4 DNA Polymerase and the MstII end with E. coli DNA Polymerase, followed by ligation; and in the second instance, by ligation alone.

Immunoprecipitation of the fusion proteins with a panel of monoclonal antibodies directed against CD4 epitopes showed that all of the epitopes were preserved. A specific high affinity association is demonstrated between the chimeric molecules and HIV envelope proteins expressed on the surface of cells transfected with an attenuated (reverse transcriptase deleted) proviral construct.

TABLE 1

```
        F  N                                  S            B
        N  S       B     M     H     DHA      S
        U  P       B     N     G     RAU      T
        4  B       V     L     A     AE9      X
        H  2       1     1     1     236      1
                                      /
    GCCTGTTTGAGAAGCAGCGGGCAAGAAAGACGCAAGCCCAGAGGCCCTGCCATTTCTGTG
  1 ---------+---------+---------+---------+---------+---------+ 60
    CGGACAAACTCTTCGTCGCCCGTTCTTTCTGCGTTCGGGTCTCCGGGACGGTAAAGACAC

B     PS             S                              S
       DBS  ADNPA     D   DHNA            M    HM         HNC
       DAP  VRLUU     D   RALU            N    AN         PRC
       EN1  AAAM9     E   AEA9            L    EL         AIF
       122  22416     1   2346            1    31         211
        /    / //         /                               /
    GGCTCAGGTCCCTACTGGCTCAGGCCCCTGCCTCCCTCGGCAAGGCCACAATGAACCGGG
 61 ---------+---------+---------+---------+---------+---------+ 120
    CCGAGTCCAGGGATGACCGAGTCCGGGGACGGAGGGAGCCGTTCCGGTGTTACTTGGCCC
```

TABLE 1-continued

```
                                              M   N   R   G -
      H                       F               F
      I           B           N       H H     N   M   D
      N           B           U       H A     U   N   D
      F           V           4       A E     4   L   E
      1           1           H       1 2     H   1   1
      GAGTCCCTTTTAGGCACTTGCTTCTGGTGCTGCAACTGGCGCTCCTCCCAGCAGCCACTC
121   ---------+---------+---------+---------+---------+---------+ 180
      CTCAGGGAAAATCCGTGAACGAAGACCACGACGTTGACCGCGAGGAGGGTCGTCGGTGAG

V   P   F   R   H   L   L   V   L   Q   L   A   L   L   P   A   A   T   Q -

B       E   E                                           R       A
          B       C   C                                           S       L
          V       0   0                                           A       U
          1       K   K                                           1       1
      AGGGAAAGAAAGTGGTGCTGGGCAAAAAAGGGGATACAGTGGAACTGACCTGTACAGCTT
181   ---------+---------+---------+---------+---------+---------+ 240
      TCCCTTTCTTTCACCACGACCCGTTTTTTCCCCTATGTCACCTTGACTGGACATGTCGAA

G   K   K   V   V   L   G   K   K   G   D   T   V   E   L   T   C   T   A   S -
                                                              H
                                                              I
                          M   M                               N
                          B   B                               F
                          0   0                               1
                          2   2
      CCCAGAAGAAGAGCATACAATTCCACTGGAAAAACTCCAACCAGATAAAGATTCTGGGAA
241   ---------+---------+---------+---------+---------+---------+ 300
      GGGTCTTCTTCTCGTATGTTAAGGTGACCTTTTTGAGGTTGGTCTATTTCTAAGACCCTT

Q   K   K   S   I   Q   F   H   W   K   N   S   N   Q   I   K   I   L   G   N -
                      B                   S               S   F   H
              N B S       F           A A           A     A   N   H   I
              L A P       D           V U           L     A   U   H   N
              A N 1       K           A 9           U     U   D   A   F
              4 2 2                   2 6           1     A   2   1   1
                /                       /
      ATCAGGGCTCCTTCTTAACTAAAGGTCCATCCAAGCTGAATGATCGCGCTGACTCAAGAA
301   ---------+---------+---------+---------+---------+---------+ 360
      TAGTCCCGAGGAAGAATTGATTTCCAGGTAGGTTCGACTTACTAGCGCGACTGAGTTCTT

Q   G   S   F   L   T   K   G   P   S   K   L   N   D   R   A   D   S   R   R -
                  S                       S           H       A           H
          M A N A S                   B A               I         A       I   D
          B V L U T                   C U               N         F       N   D
          0 A A 9 Y                   L 3               F         L       F   E
          2 2 4 6 1                   1 A               1         2       1   1
                  /                       /
      GAAGCCTTTGGGACCAAGGAAACTTCCCCCTGATCATCAAGAATCTTAAGATAGAAGACT
361   ---------+---------+---------+---------+---------+---------+ 420
      CTTCGGAAACCCTGGTTCCTTTGAAGGGGGACTAGTAGTTCTTAGAATTCTATCTTCTGA

S   L   W   D   Q   G   N   F   P   L   I   I   K   N   L   K   I   E   D   S -
                                              S
          M           M                   A M A M                   M
          B           N                   V N U N                   A
          0           L                   A L 9 L                   E
          2           1                   2 1 6 1                   1
                                              / /
      CAGATACTTACATCTGTGAAGTGGAGGACCAGAAGGAGGAGGTGCAATTGCTAGTGTTCG
421   ---------+---------+---------+---------+---------+---------+ 480
      GTCTATGAATGTAGACACTTCACCTCCTGGTCTTCCTCCTCCACGTTAACGATCACAAGC

D   T   Y   I   C   E   V   E   D   Q   K   E   E   V   Q   L   L   V   F   G -
                              B
                              S                                       S
                              P                                       T
                              M                                       Y
                              1                                       1
      GATTGACTGCCAACTCTGACACCCACCTGCTTCAGGGGCAGAGCCTGACCCTGACCTTGG
481   ---------+---------+---------+---------+---------+---------+ 540
      CTAACTGACGGTTGAGACTGTGGGTGGACGAAGTCCCCGTCTCGGACTGGGACTGGAACC
```

TABLE 1-continued

```
    L   T   A   N   S   D   T   H   L   L   Q   G   Q   S   L   T   L   T   L   E -
        B       BS                              H
        BS      SC          D           M       I       S
        AP      TR          D           N       N       T
        N1      NF          E           L       F       Y
        22      11          1           1       1       1
                /   /
        AGAGCCCCCCTGGTAGTAGCCCCTCAGTGCAATGTAGGAGTCCAAGGGGTAAAAACATAC
541     ---------+---------+---------+---------+---------+---------+ 600
        TCTCGGGGGGACCATCATCGGGGAGTCACGTTACATCCTCAGGTTCCCCATTTTTGTATG

S   P   P   G   S   S   P   S   V   Q   C   R   S   P   R   G   K   N   I   Q -
                                        N           BBH  S   B           BS
                            M   MD      ASP  A   BSSGSC  S   B   N       SC
                            B   ND      LPV  L   APTIAR  T   A   L       TR
                            0   LE      UBU  U   N1NACF  X   N   A       NF
                            2   11      122  1   221111  1   1   4       11
                                //         /   ///         /
        AGGGGGGGAAGACCCTCTCCGTGTCTCAGCTGGAGCTCCAGGATAGTGGCACCTGGACAT
601     ---------+---------+---------+---------+---------+---------+ 660
        TCCCCCCCTTCTGGGAGAGGCACAGAGTCGACCTCGAGGTCCTATCACCGTGGACCTGTA

G   G   K   T   L   S   V   S   Q   L   E   L   Q   D   S   G   T   W   T   C -
    N
    NS                                  M                           NM      A
    LP                                  B                           HA      L
    AH                                  0                           EE      U
    31                                  2                           11      1
    /
        GCACTGTCTTGCAGAACCAGAAGAAGGTGGAGTTCAAAATAGACATCGTGGTGCTAGCTT
661     ---------+---------+---------+---------+---------+---------+ 720
        CGTGACAGAACGTCTTGGTCTTCTTCCACCTCAAGTTTTATCTGTAGCACCACGATCGAA

T   V   L   Q   N   Q   K   K   V   E   F   K   I   D   I   V   V   L   A   F -
                HS              M   M
                AT              N   N
                EU              L   L
                31              1   1
                /
        TCCAGAAGGCCTCCAGCATAGTCTATAAGAAAGAGGGGAACAGGTGGAGTTCTCCTTCC
721     ---------+---------+---------+---------+---------+---------+ 780
        AGGTCTTCCGGAGGTCGTATCAGATATTCTTTCTCCCCCTTGTCCACCTCAAGAGGAAGG

Q   K   A   S   S   I   V   Y   K   K   E   G   E   Q   V   E   F   S   F   P -
                            A                   A           M
                            L                   L           N
                            U                   U           L
                            1                   1           1
        CACTCGCCTTTACAGTTGAAAAGCTGACGGGCAGTGGCGAGCTGTGGTGGCAGGCGGAGA
781     ---------+---------+---------+---------+---------+---------+ 840
        GTGAGCGGAAATGTCAACTTTTCGACTGCCCGTCACCGCTCGACACCACCGTCCGCCTCT

L   A   F   T   V   E   K   L   T   G   S   G   E   L   W   W   Q   A   E   R -
                    P   S
        H       M   FM  A                                           M
        P       N   LN  U                                           B
        H       L   ML  3                                           0
        1       1   11  A                                           2
        GGGCTTCCTCCTCCAAGTCTTGGATCACCTTTGACCTGAAGAACAAGGAAGTGTCTGTAA
841     ---------+---------+---------+---------+---------+---------+ 900
        CCCGAAGGAGGAGGTTCAGAACCTAGTGGAAACTGGACTTCTTGTTCCTTCACAGACATT

A   S   S   S   K   S   W   I   T   F   D   L   K   N   K   E   V   S   V   K -
        B           BS      PS
        SM          SCADNPAD    A                   A   H
        TA          TRVRLUUD    L                   L   P
        EE          NFAAAM9E    U                   U   H
        23          11224161    1                   1   1
        /           /  ///
        AACGGGTTACCCAGGACCCTAAGCTCCAGATGGGCAAGAAGCTCCCGCTCCACCTCACCC
901     ---------+---------+---------+---------+---------+---------+ 960
```

TABLE 1-continued

```
     TTGCCCAATGGGTCCTGGGATTCGAGGTCTACCCGTTCTTCGAGGGCGAGGTGGAGTGGG

R    V    T    Q    D    P    K    L    Q    M    G    K    K    L    P    L    H    L    T    L -

BS                                            BSS
      M    SC   HS        D              M    H          SCAHM
      N    TR   AT        D              N    P          TRUAN
      L    NF   EU        E              L    H          NF9EL
      1    11   31        1              1    1          11631
           /    /                                        /    /
     TGCCCCAGGCCTTGCCTCAGTATGCTGGCTCTGGAAACCTCACCCTGGCCCTTGAAGCGA
961  ---------+---------+---------+---------+---------+---------+  1020
     ACGGGGTCCGGAACGGAGTCATACGACCGAGACCTTTGGAGTGGGACCGGGAACTTCGCT

P    Q    A    L    P    Q    Y    A    G    S    G    N    L    T    L    A    L    E    A    K -

S         BS
                          F         SC                        H    D         A
                          A         TR                        P    D         L
                          N         NF                        H    E         U
                          1         11                        1    1         1
                                    /
     AAACAGGAAAGTTGCATCAGGAAGTGAACCTGGTGGTGATGAGAGCCACTCAGCTCCAGA
1021 ---------+---------+---------+---------+---------+---------+  1080
     TTTGTCCTTTCAACGTAGTCCTTCACTTGGACCACCACTACTCTCGGTGAGTCGAGGTCT

T    G    K    L    H    Q    E    V    N    L    V    V    M    R    A    T    Q    L    Q    K -

PS             S
      M                             ADNNPA         DF   AM        DE        A
      N                             VRLLUU         DA   LN        DS   L
      L                             AAAAM9         EN   UL        EP   U
      1                             224416         11   11        11   1
                                    /////          /    /         /
     AAAATTTGACCTGTGAGGTGTGGGGACCCACCTCCCCTAAGCTGATGCTGAGCTTGAAAC
1081 ---------+---------+---------+---------+---------+---------+  1140
     TTTTAAACTGGACACTCCACACCCCTGGGTGGAGGGGATTCGACTACGACTCGAACTTTG

N    L    T    C    E    V    W    G    P    T    S    P    K    L    M    L    S    L    K    L -

M                        T                   H              M              DM
      N                        A                   P              N              DS
      L                        Q                   A              L              ET
      1                        1                   2              1              12
                                                                                 /
     TGGAGAACAAGGAGGCAAAGGTCTCGAAGCGGGAGAAGCCGGTGTGGGTGCTGAACCCTG
1141 ---------+---------+---------+---------+---------+---------+  1200
     ACCTCTTGTTCCTCCGTTTCCAGAGCTTCGCCCTCTTCGGCCACACCCACGACTTGGGAC

E    N    K    E    A    K    V    S    K    R    E    K    P    V    W    V    L    N    P    E -

H                        PS             H
                F    D    M    I    A                   ADPA           I
                0    D    A    N    V                   VRUU           N
                K    E    E    F    A                   AAM9           F
                1    1    3    1    1                   2216           1
                                                        ///
     AGGCGGGGATGTGGCAGTGTCTGCTGAGTGACTCGGGACAGGTCCTGCTGGAATCCAACA
1201 ---------+---------+---------+---------+---------+---------+  1260
     TCCGCCCCTACACCGTCACAGACGACTCACTGAGCCCTGTCCAGGACGACCTTAGGTTGT

A    G    M    W    Q    C    L    L    S    D    S    G    Q    V    L    L    E    S    N    I -

S         SA   BHF  BS                            H
                ANA       HNCP      SGNMAANXA                     RSD  I    A
                VLU       PCRA      PIUNMULHV                     SCD  N    L
                AA9       AIFL      1ADLH3A0A                     AAE  D    U
                236       2111      21211A421                     111  3    1
                //        //        / / / /                       /
     TCAAGGTTCTGCCCACATGGTCCACCCCGGTGCACGCGGATCCCGAGGGTGAGTACTAAG
1261 ---------+---------+---------+---------+---------+---------+  1320
     AGTTCCAAGACGGGTGTACCAGGTGGGGCCACGTGCGCCTAGGGCTCCCACTCATGATTC

K    V    L    P    T    W    S    T    P    V    H    A    D    P    E

BS                                                 B
      H         H    SC   HS        S              M              M    D     S
      P         A    TR   AT        T              N              N    D     P
      H         E    NF   EU        Y              L              L    E     M
```

TABLE 1-continued

```
              1           3 11 31       1          1                 1  1  1
              /           /  /  /       /          /                 /  /  /
              CTTTCTGGGGCAGGCCAGGCCTGACCTTGGCTTTGGGGCAGGGAGGGGGCTAAGGTGAGG
         1321 ---------+---------+---------+---------+---------+---------+ 1380
              GAAAGACCCCGTCCGGTCCGGACTGGAACCGAAACCCCGTCCCTCCCCCGATTCCACTCC

B         A     BH                 B      P
                  BASHBHHNN    P     SG              N  BS     F              H
                  AHPHBAPAL    A     PI              L  AP     L              G
                  NAMAEEHRA    L     1A              A  N1     M              A
                  121112114    1     21              3  22     1              1
                      /  ////        /                  /              /
              CAGGTGGCGCCAGCAGGTGCACACCCAATGCCCATGAGCCCAGACACTGGACGCTGAACC
         1381 ---------+---------+---------+---------+---------+---------+ 1440
              GTCCACCGCGGTCGTCCACGTGTGGGTTACGGGTACTCGGGTCTGTGACCTGCGACTTGG

F               BS    S         B  SS        B  S           FN
                  N  M               SC  DNHA        H  SMAAHNABSAC              NS
                  U  N               TR  RLAU        H  TNUUALPAPLR              UP
                  D  L               NF  AAE9        A  NL99EAAN1UF              DB
                  2  1               11  2346        1  11663412211              22
                                          /            /     /// /                /
              TCGCGGACAGTTAAGAACCCAGGGGCCTCTGCGCCTGGGCCCAGCTCTGTCCCACACCGC
         1441 ---------+---------+---------+---------+---------+---------+ 1500
              AGCGCCTGTCAATTCTTGGGTCCCCGGAGACGCGGACCCGGGTCGAGACAGGGTGTGGCG

F                    BSS               BS
                  MS       BNN         NM         S  BMDMHNABSAA               SCB
                  AA       ALL         UN         T  BBRNALPAPUU               TRA
                  EC       NAA         4L         Y  V0ALEAAN199               NFN
                  32       134         H1         1  12213412266               111
                   /        /                         /  /   ////
              GGTCACATGGCACCACCTCTCTTGCAGCCTCCACCAAGGGCCCATCGGTCTTCCCCCTGG
         1501 ---------+---------+---------+---------+---------+---------+ 1560
              CCAGTGTACCGTGGTGGAGAGAACGTCGGAGGTGGTTCCCGGGTAGCCAGAAGGGGGACC
                                               A  S  T  K  G  P  S  V  F  P  L  A -

BH         B  NFS    BS       F     BS
                  N     M  MSG     MSB SNAH     SC       N     SC
                  L     N  NPI     NPB PUUA     TR       U     TR
                  A     L  L1A     L1V B49E     NF       4     NF
                  4     1  121     121 2H63     11       H     11
                                       /          /              /
              CACCCTCCTCCAAGAGCACCTCTGGGGGCACAGCGGCCCTGGGCTGCCTGGTCAAGGACT
         1561 ---------+---------+---------+---------+---------+---------+ 1620
              GTGGGAGGAGGTTCTCGTGGAGACCCCCGTGTCGCCGGGACCCGACGGACCAGTTCCTGA
                   P  S  S  K  S  T  S  G  G  T  A  A  L  G  C  L  V  K  D  Y -

NF    A     BH
                           H M     T       H       BANHBHN    SN    P     SG
                           P A     T       P    D  AHAHBAL    PU    A     PI
                           A E     H       H    D  NARAEEA    B4    L     1A
                           2 3     1       1    E  1211124    2H    1     21
                                                1                /   //         /
              ACTTCCCCGAACCGGTGACGGTGTCGTGGAACTCAGGCGCCCTGACCAGCGGCGTGCACA
         1621 ---------+---------+---------+---------+---------+---------+ 1680
              TGAAGGGGCTTGGCCACTGCCACAGCACCTTGAGTCCGCGGGACTGGTCGCCGCACGTGT
                   F  P  E  P  V  T  V  S  W  N  S  G  A  L  T  S  G  V  H  T -

S
                    HNC             DM       H              F           B
                    PCR             DS       I     M     D  N     M  SM B
                    AIF             ET       N     N     D  U     N  TA B
                    211             12       F     L     E  4     L  EE V
                     //              /       1     1     1  H     1  23 1
              CCTTCCCGGCTGTCCTACAGTCCTCAGGACTCTACTCCCTCAGCAGCGTGGTGACCGTGC
         1681 ---------+---------+---------+---------+---------+---------+ 1740
              GGAAGGGCCGACAGGATGTCAGGAGTCCTGAGATGAGGGAGTCGTCGCACCACTGGCACG
                   F  P  A  V  L  Q  S  S  G  L  Y  S  L  S  S  V  V  T  V  P -

B         F  B         B                    H
                  SH        N  ASM       B   NSB              M        I
                  PP        U  LTN       A   LPB              A        N
                  1H        4  UXL       N   A1V              E        F
                  21        H  111       1   421              2        1
                                /
              CCTCCAGCAGCTTGGGCACCCAGACCTACATCTGCAACGTGAATCACAAGCCCAGCAACA
         1741 ---------+---------+---------+---------+---------+---------+ 1800
              GGAGGTCGTCGAACCCGTGGGTCTGGATGTAGACGTTGCACTTAGTGTTCGGGTCGTTGT
```

TABLE 1-continued

```
        S   S   S   L   G   T   Q   T   Y   I   C   N   V   N   H   K   P   S   N   T -

S               M                       HM      HM
        T               N                       AN      PN
        Y               L                       EL      HL
        1               1                       31      11
     CCAAGGTGGACAAGAAAGTTGGTGAGAGGCCAGCACAGGGAGGGAGGGTGTCTGCTGGAA
1801 ---------+---------+---------+---------+---------+---------+ 1860
     GGTTCCACCTGTTCTTTCAACCACTCTCCGGTCGTGTCCCTCCCTCCCACAGACGACCTT

K   V   D   K   K   V

E           BS              SS      F           BS      F
        DE      CHH     F   SC              HHNCF   N           BSC     N
        DS      0HA     0   TR              PGCRA   U           BTR     U
        EP      4AE     K   NF              AAIFN   4           VNF     4
        11      712     1   11              21111   H           111     H
        /               /                   //                  //
     GCAGGCTCAGCGCTCCTGCCTGGACGCATCCCGGCTATGCAGCCCCAGTCCAGGGCAGCA
1861 ---------+---------+---------+---------+---------+---------+ 1920
     CGTCCGAGTCGCGAGGACGGACCTGCGTAGGGCCGATACGTCGGGGTCAGGTCCCGTCGT

S
        DBHMHNA             HMNCN                   M       MNDM
        RBABPLU             PNCRL                   N       NLDB
        AVE0HA9             ALIFA                   L       LAE0
        2132146             21114                   1       1312
        // //               //
     AGGCAGGCCCCGTCTGCCTCTTCACCCGGAGCCTCTGCCCGCCCCACTCATGCTCAGGGA
1921 ---------+---------+---------+---------+---------+---------+ 1980
     TCCGTCCGGGGCAGACGGAGAAGTGGGCCTCGGAGACGGGCGGGGTGAGTACGAGTCCCT

BS      P                       B           BS
                        SC      F               M   B   N   S       SC
                        TR      L               A   A   L   P       TR
                        NF      M               E   N   A   1       NF
                        11      1               1   1   4   2       11
                                /
     GAGGGTCTTCTGGCTTTTTCCCAGGCTCTGGGCAGGCACAGGCTAGGTGCCCCTAACCCA
1981 ---------+---------+---------+---------+---------+---------+ 2040
     CTCCCAGAAGACCGAAAAAGGGTCCGAGACCCGTCCGTGTCCGATCCACGGGGATTGGGT

S           B                   B           B               S
        DHA             S                   DBS         S       M       HNC     A
        RAU             P                   DAP         P       N       PCR     V
        AE9             M                   EN1         M       L       AIF     A
        236             1                   122         1       1       211     2
        /                                   /
     GGCCCTGCACACAAAGGGGCAGGTGCTGGGCTCAGACCTGCCAAGAGCCATATCCGGGAG
2041 ---------+---------+---------+---------+---------+---------+ 2100
     CCGGGACGTGTGTTTCCCCGTCCACGACCCGAGTCTGGACGGTTCTCGGTATAGGCCCTC

PS
        DNPA        D               H               D       A       M
        RLUU        D               A               D       L       N
        AAM9        E               E               E       U       L
        2416        1               3               1       1       1
        / //
     GACCCTGCCCCTGACCTAAGCCCACCCCAAAGGCCAAACTCTCCACTCCCTCAGCTCGGA
2101 ---------+---------+---------+---------+---------+---------+ 2160
     CTGGGACGGGGACTGGATTCGGGTGGGGTTTCCGGTTTGAGAGGTGAGGGAGTCGAGCCT

H                                   B
                        I   M   MM                      P       BS
                        N   N   AB                      S       AP
                        F   L   E0                      T       N1
                        1   1   32                      1       22
                                /                               /
     CACCTTCTCTCCTCCCAHATTCCAHTAACTCCCAATCTTCTCTCHCAHACCCAAATCT
2161 ---------+---------+---------+---------+---------+---------+ 2220
     GTGGAAGAGAGGAGGGTCTAAGGTCATTGAGGGTTAGAAGAGAGACGTCTCGCCTTTACA

E   P   K   S -

N           BBS             BS
        M               NS          SSC             SC  HS              M
        A               LP          PTR             TR  AT              N
        E               AH          1NF             NF  EU              L
        3               31          211             11  31              1
```

TABLE 1-continued

```
                       /            /          //     /
     TGTGACAAAACTCACACATGCCCACCGTGCCCAGGTAAGCCAGCCCAGGCCTCGCCCTCC
2221 ---------+---------+---------+---------+---------+---------+ 2280
     ACACTGTTTTGAGTGTGTACGGGTGGCACGGGTCCATTCGGTCGGGTCCGGAGCGGGAGG
      C  D  K  T  H  T  C  P  P  C  P

B                   BS S        S       S
         A     M          B  N  SM F             SC F      DHNA    HNC
         L     N          A  L  PA 0             TR A      RALU    PCR
         U     L          N  A  1E K             NF N      AEA9    AIF
         1     1          1  4  21 1             11 1      2346    211
                                                    /       /       /
     AGCTCAAGGCGGGACAGGTGCCCTAGAGTAGCCTGCATCCAGGGACAGGCCCCAGCCGGG
2281 ---------+---------+---------+---------+---------+---------+ 2340
     TCGAGTTCCGCCCTGTCCACGGGATCTCATCGGACGTAGGTCCCTGTCCGGGGTCGGCCC

BS        S
           A M   M                  M   D       M    SC  M  ANA M
           F A   B                  N   D       N    TR  B  VLU B
           L E   0                  L   E       L    NF  0  AA9 0
           3 2   2                  1   1       1    11  2  246 2
                                                        /     /
     TGCTGACACGTCCACCTCCATCTCTTCCTCAGCACCTGAACTCCTGGGGGGACCGTCAGT
2341 ---------+---------+---------+---------+---------+---------+ 2400
     ACGACTGTGCAGGTGGAGGTAGAGAAGGAGTCGTGGACTTGAGGACCCCCCTGGCAGTCA
                                              A  P  E  L  L  G  G  P  S  V -

S              SS
                M     S              AN    M HMANNAC DM  M
                N     T              UL    N PNVCLUR DS  A
                L     Y              3A    L ALAIA9F ET  E
                1     1              A3    1 2121461 12  3
                                        /   /// /
     CTTCCTCTTCCCCCCAAAACCCAAGGACACCCTCATGATCTCCCGGACCCCTGAGGTCAC
2401 ---------+---------+---------+---------+---------+---------+ 2460
     GAAGGAGAAGGGGGGTTTTGGGTTCCTGTGGGACTACTAGAGGGCCTGGGGACTCCAGTG
      F  L  F  P  P  K  P  K  D  T  L  M  I  S  R  T  P  E  V  T -

N
        NS              M         M     DM    M                RM    M
        LP              A         N     DS    B                SA    N
        AH              E         L     ET    0                AE    L
        31              2         1     12    2                12    1
         /                                /
     ATGCGTGGTGGTGGACGTGAGCCACGAAGACCCTGAGGTCAAGTTCAACTGGTACGTGGA
2461 ---------+---------+---------+---------+---------+---------+ 2520
     TACGCACCACCACCTGCACTCGGTGCTTCTGGGACTCCAGTTCAAGTTGACCATGCACCT
      C  V  V  V  D  V  S  H  E  D  P  E  V  K  F  N  W  Y  V  D -

F  FN
                               M N  NSS        R         M    R
                               N U  UPA        S         A    S
                               L 4  DBC        A         E    A
                               1 H  222        1         2    1
                                      //
     CGGCGTGGAGGTGCATAATGCCAAGACAAAGCCGCGGGAGGAGCAGTACAACAGCACGTA
2521 ---------+---------+---------+---------+---------+---------+ 2580
     GCCGCACCTCCACGTATTACGGTTCTGTTTCGGCGCCCTCCTCGTCATGTTGTCGTGCAT
      G  V  E  V  H  N  A  K  T  K  P  R  E  E  Q  Y  N  S  T  Y -

S                         BS
       HNC HH                 M      SC                     R
       PCR GP                 N      TR                     S
       AIF AH                 L      NF                     A
       211 11                 1      11                     1
        /                            /
     CCGGGTGGTCAGCGTCCTCACCGTCCTGCACCAGGACTGGCTGAATGGCAAGGAGTACAA
2581 ---------+---------+---------+---------+---------+---------+ 2640
     GGCCCACCAGTCGCAGGAGTGGCAGGACGTGGTCCTGACCGACTTACCGTTCCTCATGTT
      R  V  V  S  V  L  T  V  L  H  Q  D  W  L  N  G  K  E  Y  K -

M    T
                                        N    A
                                        L    Q
```

TABLE 1-continued

```
                              1   1
     GTGCAAGGTCTCCAACAAAGCCCTCCCAGCCCCCATCGAGAAAACCATCTCCAAAGCCAA
2641 ---------+---------+---------+---------+---------+---------+ 2700
     CACGTTCCAGAGGTTGTTTCGGGAGGGTCGGGGGTAGCTCTTTTGGTAGAGGTTTCGGTT
      C  K  V  S  N  K  A  L  P  A  P  I  E  K  T  I  S  K  A  K  -

P S              S
          ADNNPMA         A H M   N        HHN    BSAH
          VRLLUNU         U A N   L        APA    GFUA
          AAAAML9         9 E L   A        EAE    LI9E
          2244116         6 3 1   3        321    1163
          //// /                                    /
     AGGTGGGACCCGTGGGGTGCGAGGGCCACATGGACAGAGGCCGGCTCGGCCCACCCTCTG
2701 ---------+---------+---------+---------+---------+---------+ 2760
     TCCACCCTGGGCACCCCACGCTCCCGGTGTACCTGTCTCCGGCCGAGCCGGGTGGGAGAC

N                   F
      D M M     S   R            M    N   A      B
      D N A     P   S            N    U   V      B
      E L E     B   A            L    4   A      V
      1 1 3    2   1             1    H   1      1
     CCCTGAGAGTGACCGCTGTACCAACCTCTGTCCTACAGGGCAGCCCCGAGAACCACAGGT
2761 ---------+---------+---------+---------+---------+---------+ 2820
     GGGACTCTCACTGGCGACATGGTTGGAGACAGGATGTCCCGTCGGGGCTCTTGGTGTCCA

G  Q  P  R  E  P  Q  V  -

SS               BS                  BS
      R F     AHNNCCS    A    F    SC                  SC
      S 0     VPCCRRM    L    0    TR                  TR
      A K     AAIIFFA    U    K    NF                  NF
      1 1     1211111    1    1    11                  11
              /////                /                   /
     GTACACCCTGCCCCCATCCCGGGATGAGCTGACCAAGAACCAGGTCAGCCTGACCTGCCT
2821 ---------+---------+---------+---------+---------+---------+ 2880
     CATGTGGGACGGGGGTAGGGCCCTACTCGACTGGTTCTTGGTCCAGTCGGACTGGACGGA

Y  T  L  P  P  S  R  D  E  L  T  K  N  Q  V  S  L  T  C  L  -

B                                        F
      S                                        N H
      P                                        U P
      M                                        4 A
      1                                        H 2
     GGTCAAAGGCTTCTATCCCAGCGACATCGCCGTGGAGTGGGAGAGCAATGGGCAGCCGGA
2881 ---------+---------+---------+---------+---------+---------+ 2940
     CCAGTTTCCGAAGATAGGGTCGCTGTAGCGGCACCTCACCCTCTCGTTACCCGTCGGCCT

V  K  G  F  Y  P  S  D  I  A  V  E  W  E  S  N  G  Q  P  E  -
                                H
      B               M I   M        N                H
      B               N N   B        L                P
      V               L F   0        A                H
      1               1 1   2        4                1
     GAACAACTACAAGACCACGCCTCCCGTGCTGGACTCCGACGGCTCCTTCTTCCTCTACAG
2941 ---------+---------+---------+---------+---------+---------+ 3000
     CTTGTTGATGTTCTGGTGCGGAGGGCACGACCTGAGGCTGCCGAGGAAGAAGGAGATGTC

N  N  Y  K  T  T  P  P  V  L  D  S  D  G  S  F  F  L  Y  S  -

B           F                   S
      M A           S           NM         MBX       NF  M
      N L           P           UB         ABM       LA  N
      L U           M           40         EVN       AN  L
      1 1           1           H2         211       31  1
                                                         /
     CAAGCTCACCGTGGACAAGAGCAGGTGGCAGCAGGGGAACGTCTTCTCATGCTCCGTGAT
3001 ---------+---------+---------+---------+---------+---------+ 3060
     GTTCGAGTGGCACCTGTTCTCGTCCACCGTCGTCCCCTTGCAGAAGAGTACGAGGCACTA

K  L  T  V  D  K  S  R  W  Q  Q  G  N  V  F  S  C  S  V  M  -

S
      N N                              M    M   HNC
      S L                              B    N   PCR
      I A                              0    L   AIF
      1 3                              2    1   211
                                                   /
```

TABLE 1-continued

```
      GCATGAGGCTCTGCACAACCACTACACGCAGAAGAGCCTCTCCCTGTCTCCGGGTAAATG
3061  ---------+---------+---------+---------+---------+---------+ 3120
      CGTACTCCGAGACGTGTTGGTGATGTGCGTCTTCTCGGAGAGGGACAGAGGCCCATTTAC

H   E   A   L   H   N   H   Y   T   Q   K   S   L   S   L   S   P   G   K   *

CXHHN
               FMAPA
               RAEAE
               13321
                 /
      AGTGCGACGGCCG
3121  ---------+--- 3133
      TCACGCTGCCGGC
```

TABLE 2

```
                      F   N                                S               B
                      N   S           B       M       H    DHA             S
                      U   P           B       N       G    RAU             T
                      4   B           V       L       A    AE9             X
                      H   2           1       1       1    236             1
                                                            /
      GCCTGTTTGAGAAGCAGCGGGCAAGAAAGACGCAAGCCCAGAGGCCCTGCCATTTCTGTG
  1   ---------+---------+---------+---------+---------+---------+ 60
      CGGACAAACTCTTCGTCGCCCGTTCTTTCTGCGTTCGGGTCTCCGGGACGGTAAAGACAC

B       PS                S                                     S
          DBS     ADNPA        D    DHNA                  M    HM          HNC
          DAP     VRLUU        D    RALU                  N    AN          PCR
          EN1     AAAM9        E    AEA9                  L    EL          AIF
          122     22416        1    2346                  1    31          211
           / /    / / /             /                                      /
      GGCTCAGGTCCCTACTGGCTCAGGCCCCTGCCTCCCTCGGCAAGGCCACAATGAACCGGG
 61   ---------+---------+---------+---------+---------+---------+ 120
      CCGAGTCCAGGGATGACCGAGTCCGGGACGGAGGGAGCCGTTCCGGTGTTACTTGGCCC

M   N   R   G -

H                           F                       F
          I               B           N           HH          N   M       D
          N               B           U           HA          U   N       D
          F               V           4           AE          4   L       E
          1               1           H           12          H   1       1
      GAGTCCCTTTTAGGCACTTGCTTCTGGTGCTGCAACTGGCGCTCCTCCCAGCAGCCACTC
121   ---------+---------+---------+---------+---------+---------+ 180
      CTCAGGGAAAATCCGTGAACGAAGACCACGACGTTGACCGCGAGGAGGGTCGTCGGTGAG

V   P   F   R   H   L   L   L   V   L   Q   L   A   L   L   P   A   A   T   Q -

B       E   E                                           R       A
           B       C   C                                           S       L
           V       D   D                                           A       U
           1       K   K                                           1       1
      AGGGAAAGAAAGTGGTGCTGGGCAAAAAAGGGGATACAGTGGAACTGACCTGTACAGCTT
181   ---------+---------+---------+---------+---------+---------+ 240
      TCCCTTTCTTTCACCACGACCCGTTTTTTCCCCTATGTCACCTTGACTGGACATGTCGAA

G   K   K   V   V   L   G   K   K   G   D   T   V   E   L   T   C   T   A   S -

H
                       M   M                          I
                       B   B                          N
                       0   0                          F
                       2   2                          1
      CCCAGAAGAAGAGCATACAATTCCACTGGAAAAACTCCAACCAGATAAAGATTCTGGGAA
241   ---------+---------+---------+---------+---------+---------+ 300
      GGGTCTTCTTCTCGTATGTTAAGGTGACCTTTTTGAGGTTGGTCTATTTCTAAGACCCTT

Q   K   K   S   I   Q   F   H   W   K   N   S   N   Q   I   K   I   L   G   N -

B               S               S   F       H
               NBS         F   AA          A    A   N   H  I
               LAP         0   VU          L    U   U   H  N
               AN1         K   A9          U    3   D   A  F
               422         1   26          1    A   2   1  1
```

TABLE 2-continued

```
                  /               /
       ATCAGGGCTCCTTCTTAACTAAAGGTCCATCCAAGCTGAATGATCGCGCTGACTCAAGAA
   301 ---------+---------+---------+---------+---------+---------+ 360
       TAGTCCCGAGGAAGAATTGATTTCCAGGTAGGTTCGACTTACTAGCGCGACTGAGTTCTT
        Q  G  S  F  L  T  K  G  P  S  K  L  N  D  R  A  D  S  R  R -

S
              MANAS           BA       H       A            H
              BVLUT           CU       I       F            I D
              0AA9Y           L3       N       L            N D
              22461           1A       F       2            F E
                                       1                    1 1
                  /               /
       GAAGCCTTTGGGACCAAGGAAACTTCCCCCTGATCATCAAGAATCTTAAGATAGAAGACT
   361 ---------+---------+---------+---------+---------+---------+ 420
       CTTCGGAAACCCTGGTTCCTTTGAAGGGGGACTAGTAGTTCTTAGAATTCTATCTTCTGA
        S  L  W  D  Q  G  N  F  P  L  I  I  K  N  L  K  I  E  D  S -

S
                                AMAM
              M      M          VNUN                     M
              B      N          AL9L                     A
              0      L          2161                     E
              2      1                                   1
                                    //
       CAGATACTTACATCTGTGAAGTGGAGGACCAGAAGGAGGAGGTGCAATTGCTAGTGTTCG
   421 ---------+---------+---------+---------+---------+---------+ 480
       GTCTATGAATGTAGACACTTCACCTCCTGGTCTTCCTCCTCCACGTTAACGATCACAAGC
        D  T  Y  I  C  E  V  E  D  Q  K  E  E  V  Q  L  L  V  F  G -

B
                                         S
                                         P                     S
                                         M                     T
                                         1                     Y
                                                               1
       GATTGACTGCCAACTCTGACACCCACCTGCTTCAGGGGCAGAGCCTGACCCTGACCTTGG
   481 ---------+---------+---------+---------+---------+---------+ 540
       CTAACTGACGGTTGAGACTGTGGGTGGACGAAGTCCCCGTCTCGGACTGGGACTGGAACC
        L  T  A  N  S  D  T  H  L  L  Q  G  Q  S  L  T  L  T  L  E -

B    BS                            H
              BS   SC          D           M     I     S
              AP   TR          D           N     N     T
              N1   NF          E           L     F     Y
              22   11          1           1     1     1
                /  /
       AGAGCCCCCCTGGTAGTAGCCCCTCAGTGCAATGTAGGAGTCCAAGGGGTAAAAACATAC
   541 ---------+---------+---------+---------+---------+---------+ 600
       TCTCGGGGGGACCATCATCGGGGAGTCACGTTACATCCTCAGGTTCCCCATTTTTGTATG
        S  P  P  G  S  S  P  S  V  Q  C  R  S  P  R  G  K  N  I  Q -

N         BBH S     B          BS
              M    MD           ASP    A  BSSGSC    S   B  N   SC
              B    ND           LPV    L  APTIAR    T   A  L   TR
              0    LE           UBU    U  N1NACF    X   N  A   NF
              2    11           122    1  221111    1      4   11
                                 //        / ///                 /
       AGGGGGGGAAGACCCTCTCCGTGTCTCAGCTGGAGCTCCAGGATAGTGGCACCTGGACAT
   601 ---------+---------+---------+---------+---------+---------+ 660
       TCCCCCCCTTCTGGGAGAGGCACAGAGTCGACCTCGAGGTCCTATCACCGTGGACCTGTA
        G  G  K  T  L  S  V  S  Q  L  E  L  Q  D  S  G  T  W  T  C -

N
        NS                          M                    NM   A
        LP                          B                    HA   L
        AH                          0                    EE   U
        31                          2                    11   1
         /
       GCACTGTCTTGCAGAACCAGAAGAAGGTGGAGTTCAAAATAGACATCGTGGTGCTAGCTT
   661 ---------+---------+---------+---------+---------+---------+ 720
       CGTGACAGAACGTCTTGGTCTTCTTCCACCTCAAGTTTTATCTGTAGCACCACGATCGAA
        T  V  L  Q  N  Q  K  K  V  E  F  K  I  D  I  V  V  L  A  F -

HS         M     M
                    AT         N     N
                    EU         L     L
                    31         1     1
                     /
       TCCAGAAGGCCTCCAGCATAGTCTATAAGAAAGAGGGGAACAGGTGGAGTTCTCCTTCC
   721 ---------+---------+---------+---------+---------+---------+ 780
```

TABLE 2-continued

```
     AGGTCTTCCGGAGGTCGTATCAGATATTCTTTCTCCCCCTTGTCCACCTCAAGAGGAAGG

Q  K  A  S  S  I  V  Y  K  K  E  G  E  Q  V  E  F  S  F  P -
                                  A           A        M
                                  L           L        N
                                  U           U        L
                                  1           1        1
     CACTCGCCTTTACAGTTGAAAAGCTGACGGGCAGTGGCGAGCTGTGGTGGCAGGCGGAGA
 781 ---------+---------+---------+---------+---------+---------+ 840
     GTGAGCGGAAATGTCAACTTTTCGACTGCCCGTCACCGCTCGACACCACCGTCCGCCTCT

L  A  F  T  V  E  K  L  T  G  S  G  E  L  W  W  Q  A  E  R -
                           P  S
                    H    M FM A                        M
                    P    N LN U                        B
                    H    L ML 3                        0
                    1    1 11 A                        2
     GGGCTTCCTCCTCCAAGTCTTGGATCACCTTTGACCTGAAGAACAAGGAAGTGTCTGTAA
 841 ---------+---------+---------+---------+---------+---------+ 900
     CCCGAAGGAGGAGGTTCAGAACCTAGTGGAAACTGGACTTCTTGTTCCTTCACAGACATT

A  S  S  S  K  S  W  I  T  F  D  L  K  N  K  E  V  S  V  K -
            B        BS   PS
            SM       SCADNPAD       A              A H
            TA       TRVRLUUD       L              L P
            EE       NFAAAM9E       U              U H
            23       11224161       1              1 1
               /        / / //
     AACGGGTTACCCAGGACCCTAAGCTCCAGATGGGCAAGAAGCTCCCGCTCCACCTCACCC
 901 ---------+---------+---------+---------+---------+---------+ 960
     TTGCCCAATGGGTCCTGGGATTCGAGGTCTACCCGTTCTTCGAGGGCGAGGTGGAGTGGG

R  V  T  Q  D  P  K  L  Q  M  G  K  K  L  P  L  H  L  T  L -
               BS                                       BSS
         M     SC HS   D       M  H                     SCAHM
         N     TR AT   D       N  P                     TRUAN
         L     NF EU   E       L  H                     NF9EL
         1     11 31   1       1  1                     11631
                / /                                       / /
     TGCCCCAGGCCTTGCCTCAGTATGCTGGCTCTGGAAACCTCACCCTGGCCCTTGAAGCGA
 961 ---------+---------+---------+---------+---------+---------+ 1020
     ACGGGGTCCGGAACGGAGTCATACGACCGAGACCTTTGGAGTGGGACCGGGAACTTCGCT

P  Q  A  L  P  Q  Y  A  G  S  G  N  L  T  L  A  E  A  K -
                           S      BS
                           F      SC                H D    A
                           A      TR                P D    L
                           N      NF                H E    U
                           1      11                1 1    1
                                   /
     AAACAGGAAAGTTGCATCAGGAAGTGAACCTGGTGGTGATGAGAGCCACTCAGCTCCAGA
1021 ---------+---------+---------+---------+---------+---------+ 1080
     TTTGTCCTTTCAACGTAGTCCTTCACTTGGACCACCACTACTCTCGGTGAGTCGAGGTCT

T  G  K  L  H  Q  E  V  N  L  V  V  M  R  A  T  Q  L  Q  K -
                           PS         S
                M          ADNNPA     DF  AM         DE    A
                N          VRLLUU     DA  LN         DS    L
                L          AAAAM9     EN  UL         EP    U
                1          224416     11  11         11    1
                           /////       /   /          /
     AAAATTTGACCTGTGAGGTGTGGGGACCCACCTCCCCTAAGCTGATGCTGAGCTTGAAAC
1081 ---------+---------+---------+---------+---------+---------+ 1140
     TTTTAAACTGGACACTCCACACCCCTGGGTGGAGGGGATTCGACTACGACTCGAACTTTG

N  L  T  C  E  V  W  G  P  T  S  P  K  L  M  L  S  L  K  L -
                M              T           H        M         DM
                N              A           P        N         DS
                L              Q           A        L         ET
                1              1           2        1         12
                                                                /
     TGGAGAACAAGGAGGCAAAGGTCTCGAAGCGGGAGAAGCCGGTGTGGGTGCTGAACCCTG
1141 ---------+---------+---------+---------+---------+---------+ 1200
     ACCTCTTGTTCCTCCGTTTCCAGAGCTTCGCCCTCTTCGGCCACACCCACGACTTGGGAC

E  N  K  E  A  K  V  S  K  R  E  K  P  V  W  V  L  N  P  E -
```

TABLE 2-continued

```
                            H              PS         H
              F      D   M  I A            ADPA       I
              0      D   A  N V            VRUU       N
              K      E   E  F A            AAM9       F
              1      1   3  1 1            2216       1
                                           ///
     AGGCGGGGATGTGGCAGTGTCTGCTGAGTGACTCGGGACAGGTCCTGCTGGAATCCAACA
1201 ---------+---------+---------+---------+---------+---------+ 1260
     TCCGCCCCTACACCGTCACAGACGACTCACTGAGCCCTGTCCAGGACGACCTTAGGTTGT

A  G  M  W  Q  C  L  L  S  D  S  G  Q  V  L  L  E  S  N  I -

S           SA    BHF BS
                   ANA         HNCP    SGNMAANXA           RSD I A
                   VLU         PCRA    PIUNMULHV           SCD N L
                   AA9         AIFL    1ADLH3ADA           AAE D U
                   236         2111    21211A421           111 3 1
                    //          //      / / / /
     TCAAGGTTCTGCCCACATGGTCCACCCCGGTGCACGCGGATCCCGAGGGTGAGTACTAAG
1261 ---------+---------+---------+---------+---------+---------+ 1320
     AGTTCCAAGACGGGTGTACCAGGTGGGGCCACGTGCGCCTAGGGCTCCCACTCATGATTC

K  V  L  P  T  W  S  T  P  V  H  A  D  P  E

E        BS             SS     F           BS    F
         H     CHH   F   SC            HHNCF   N           BSC   N
         P     0HA   0   TR            PGCRA   U           BTR   U
         H     4AE   K   NF            AAIFN   4           VNF   4
         1     712   1   11            21111   H           111   H
         /              /               //                  //
     CTTCAGCGCTCCTGCCTGGACGCATCCCGGCTATGCAGCCCCAGTCCAGGGCAGCAAGGC
1321 ---------+---------+---------+---------+---------+---------+ 1380
     GAAGTCGCGAGGACGGACCTGCGTAGGGCCGATACGTCGGGGTCAGGTCCCGTCGTTCCG

S                    S
        DBHMHNA              HMVCN         M       MNDM
        RBABPLU              PNCRL         N       NLDB
        AVE0HA9              ALIFA         L       LAE0
        2132146              21114         1       1312
         // //                //
     AGGCCCCGTCTGCCTCTTCACCCGGAGCCTCTGCCCGCCCCACTCATGCTCAGGGAGAGG
1381 ---------+---------+---------+---------+---------+---------+ 1440
     TCCGGGGCAGACGGAGAAGTGGGCCTCGGAGACGGGCGGGGTGAGTACGAGTCCCTCTCC

BS    P                     B       BS   S
                     SC    F           M  B  N   S       SCDHA
                     TR    L           A  A  L   P       TRRAU
                     NF    M           E  N  A   1       NFAE9
                     11    1           1  1  4   2       11236
                      /                                   / /
     GTCTTCTGGCTTTTTCCCAGGCTCTGGGCAGGCACAGGCTAGGTGCCCCTAACCCAGGCC
1441 ---------+---------+---------+---------+---------+---------+ 1500
     CAGAAGACCGAAAAAGGGTCCGAGACCCGTCCGTGTCCGATCCACGGGGATTGGGTCCGG

B                 B              B               S
         S                    DBS             S   M          HNC    ADNPA
         P                    DAP             P   N          PCR    VRLUU
         M                    EN1             M   L          AIF    AAAM9
         1                    122             1   1          211    22416
                               /                              /      ///
     CTGCACACAAAGGGGCAGGTGCTGGGCTCAGACCTGCCAAGAGCCATATCCGGGAGGACC
1501 ---------+---------+---------+---------+---------+---------+ 1560
     GACGTGTGTTTCCCCGTCCACGACCCGAGTCTGGACGGTTCTCGGTATAGGCCCTCCTGG

D                H              D    A    M
                  D                A              D    L    N
                  E                E              E    U    L
                  1                3              1    1    1
     CTGCCCCTGACCTAAGCCCACCCCAAAGGCCAAACTCTCCACTCCCTCAGCTCGGACACC
1561 ---------+---------+---------+---------+---------+---------+ 1620
     GACGGGGACTGGATTCGGGTGGGGTTTCCGGTTTGAGAGGTGAGGGAGTCGAGCCTGTGG

H                                       B
             I  M  MM                          P    BS    M
             N  N  AB                          S    AP    A
             F  L  E0                          T    N1    E
             1  1  32                          1    22    3
                 /                                           /
```

TABLE 2-continued

```
      TTCTCTCCTCCCAGATTCCAGTAACTCCCAATCTTCTCTCTGCAGAGCCCAAATCTTGTG
1621  ---------+---------+---------+---------+---------+---------+ 1680
      AAGAGAGGAGGGTCTAAGGTCATTGAGGGTTAGAAGAGAGACGTCTCGGGTTTAGAACAC

E  P  K  S  C  D  -

M  A
                 N          BBS              BS          N  L
                 NS         SSC              SC  HS      L  U
                 LP         PTR              TR  AT      1  1
                 AH         1NF              NF  EU
                 31         211              11  31
                 /          /                /   /
      ACAAAACTCACACATGCCCACCGTGCCCAGGTAAGCCAGCCCAGGCCTCGCCCTCCAGCT
1681  ---------+---------+---------+---------+---------+---------+ 1740
      TGTTTTGAGTGTGTACGGGTGGCACGGGTCCATTCGGTCGGGTCCGGAGCGGGAGGTCGA

K  T  H  T  C  P  P  C  P

B                    BS  S          S
          M        B  N  SM F                  SC  F    DHNA HNC
          N        A  L  PA 0                  TR  A    RALU PCR
          L        N  A  1E K                  NF  N    AEA9 AIF
          1        1  4  21 1                  11  1    2346 211
                         /                     /        /
      CAAGGCGGGACAGGTGCCCTAGAGTAGCCTGCATCCAGGGACAGGCCCCAGCCGGGTGCT
1741  ---------+---------+---------+---------+---------+---------+ 1800
      GTTCCGCCCTGTCCACGGGATCTCATCGGACGTAGGTCCCTGTCCGGGGTCGGCCCACGA

BS        S
       A  M  M           M  D           M     SC  M ANA M
       F  A  B           N  D           N     TR  B VLU B
       L  E  0           L  E           L     NF  0 AA9 0
       3  2  2           1  1           1     11  2 246 2
                                              /     /
      GACACGTCCACCTCCATCTCTTCCTCAGCACCTGAACTCCTGGGGGACCGTCAGTCTTC
1801  ---------+---------+---------+---------+---------+---------+ 1860
      CTGTGCAGGTGGAGGTAGAGAAGGAGTCGTGGACTTGAGGACCCCCCTGGCAGTCAGAAG

A  P  E  L  L  G  G  P  S  V  F  -

S                 SS              N
         M        S            AN   M HMANNAC DM  M            NS
         N        T            UL   N PNVCLUR DS  A            LP
         L        Y            3A   L ALAIA9F ET  E            AH
         1        1            A3   1 2121461 12  3            31
                               /     / /// /               /
      CTCTTCCCCCCAAAACCCAAGGACACCCTCATGATCTCCCGGACCCCTGAGGTCACATGC
1861  ---------+---------+---------+---------+---------+---------+ 1920
      GAGAAGGGGGGTTTTGGGTTCCTGTGGGAGTACTAGAGGGCCTGGGGACTCCAGTGTACG

L  F  P  P  K  P  K  D  T  L  M  I  S  R  T  P  E  V  T  C  -

M           M      DM   M           RM     M
                A           N      DS   B           SA     N
                E           L      ET   0           AE     L
                2           1      12   2           12     1
                                   /
      GTGGTGGTGGACGTGAGCCACGAAGACCCTGAGGTCAAGTTCAACTGGTACGTGGACGGC
1921  ---------+---------+---------+---------+---------+---------+ 1980
      CACCACCACCTGCACTCGGTGCTTCTGGGACTCCAGTTCAAGTTGACCATGCACCTGCCG

V  V  V  D  V  S  H  E  D  P  E  V  K  F  N  W  Y  V  D  G  -

F  FN                              S
                   M        N  NSS              R        M  R  HNC
                   N        U  UPA              S        A  S  PCR
                   L        4  DBC              A        E  A  AIF
                   1        H  222              1        2  1  211
                               //                                /
      GTGGAGGTGCATAATGCCAAGACAAAGCCGCGGGAGGAGCAGTACAACAGCACGTACCGG
1981  ---------+---------+---------+---------+---------+---------+ 2040
      CACCTCCACGTATTACGGTTCTGTTTCGGCGCCCTCCTCGTCATGTTGTCGTGCATGGCC

V  E  V  H  N  A  K  T  K  P  R  E  E  Q  Y  N  S  T  Y  R  -

BS
              HH              M      SC                R
              GP              N      TR                S
              AH              L      NF                A
```

TABLE 2-continued

```
         11                    1    11                                 1
                                     /
         GTGGTCAGCGTCCTCACCGTCCTGCACCAGGACTGGCTGAATGGCAAGGAGTACAAGTGC
    2041 ---------+---------+---------+---------+---------+---------+ 2100
         CACCAGTCGCAGGAGTGGCAGGACGTGGTCCTGACCGACTTACCGTTCCTCATGTTCACG

V  V  S  V  L  T  V  L  H  Q  D  W  L  N  G  K  E  Y  K  C   -

M  T
                                      N  A
                                      L  Q
                                      1  1
         AAGGTCTCCAACAAAGCCCTCCCAGCCCCCATCGAGAAAACCATCTCCAAAGCCAAAGGT
    2101 ---------+---------+---------+---------+---------+---------+ 2160
         TTCCAGAGGTTGTTTCGGGAGGGTCGGGGGTAGCTCTTTTGGTAGAGGTTTCGGTTTCCA

K  V  S  N  K  A  L  P  A  P  I  E  K  T  I  S  K  A  K

P  S        S                                S
           ADNNPMA      A H M     N         HHN    BSAH              D
           VRLLUNU      U A N     L         APA    GFUA              D
           AAAAML9      9 E L     A         EAE    LI9E              E
           2244116      6 3 1     3         321    1163              1
            ////         /                                 /
         GGGACCCGTGGGGTGCGAGGGCCACATGGACAGAGGCCGGCTCGGCCCACCCTCTGCCCT
    2161 ---------+---------+---------+---------+---------+---------+ 2220
         CCCTGGGCACCCCACGCTCCCGGTGTACCTGTCTCCGGCCGAGCCGGGTGGGAGACGGGA

N                         F
          M  M     S  R              M  N    A  B             R  F
          N  A     P  S              N  U    V  B             S  0
          L  E     B  A              L  4    A  V             A  K
          1  3     2  1              1  H    1  1             1  1
         GAGAGTGACCGCTGTACCAACCTCTGTCCTACAGGGCAGCCCCGAGAACCACAGGTGTAC
    2221 ---------+---------+---------+---------+---------+---------+ 2280
         CTCTCACTGGCGACATGGTTGGAGACAGGATGTCCCGTCGGGGCTCTTGGTGTCCACATG

G  Q  P  R  E  P  Q  V  Y   -

SS                   BS                   BS  B
                 AHNNCCS     A     F    SC                   SC  S
                 VPCCRRM     L     0    TR                   TR  P
                 AAIIFFA     U     K    NF                   NF  M
                 1211111     1     1    11                   11  1
                  /////                  /                        /
         ACCCTGCCCCCATCCCGGGATGAGCTGACCAAGAACCAGGTCAGCCTGACCTGCCTGGTC
    2281 ---------+---------+---------+---------+---------+---------+ 2340
         TGGGACGGGGGTAGGGCCCTACTCGACTGGTTCTTGGTCCAGTCGGACTGGACGGACCAG

T  L  P  P  S  R  D  E  L  T  K  N  Q  V  S  L  T  C  L  V   -

F
                                        N   H                B
                                        U   P                B
                                        4   A                V
                                        H   2                1
         AAAGGCTTCTATCCCAGCGACATCGCCGTGGAGTGGGAGAGCAATGGGCAGCCGGAGAAC
    2341 ---------+---------+---------+---------+---------+---------+ 2400
         TTTCCGAAGATAGGGTCGCTGTAGCGGCACCTCACCCTCTCGTTACCCGTCGGCCTCTTG

K  G  F  Y  P  S  D  I  A  V  E  W  E  S  N  G  Q  P  E  N   -

H
               M  I       M           N              H        M  A
               N  N       B           L              P        N  L
               L  F       0           A              H        L  U
               1  1       2           4              1        1  1
         AACTACAAGACCACGCCTCCCGTGCTGGACTCCGACGGCTCCTTCTTCCTCTACAGCAAG
    2401 ---------+---------+---------+---------+---------+---------+ 2460
         TTGATGTTCTGGTGCGGAGGGCACGACCTGAGGCTGCCGAGGAAGAAGGAGATGTCGTTC

N  Y  K  T  T  P  P  V  L  D  S  D  G  S  F  F  L  Y  S  K   -

B            F                        S
                     S           NM          MBX           NF  M        N
                     P           UB          ABM           LA  N        I
                     M           40          EVN           AN  L        I
                     1           H2          211           31  1        1
                                                            /
```

TABLE 2-continued

```
      CTCACCGTGGACAAGAGCAGGTGGCAGCAGGGGAACGTCTTCTCATGCTCCGTGATGCAT
2461  ---------+---------+---------+---------+---------+---------+ 2520
      GAGTGGCACCTGTTCTCGTCCACCGTCGTCCCCTTGCAGAAGAGTACGAGGCACTACGTA

L  T  V  D  K  S  R  W  Q  Q  G  N  V  F  S  C  S  V  M  H  -

S
      N                                         M     M    HNC
      L                                         B     N    PCR
      A                                         0     L    AIF
      3                                         2     1    211
                                                            /
      GAGGCTCTGCACAACCACTACACGCAGAAGAGCCTCTCCCTGTCTCCGGGTAAATGAGTG
2521  ---------+---------+---------+---------+---------+---------+ 2580
      CTCCGAGACGTGTTGGTGATGTGCGTCTTCTCGGAGAGGGACAGAGGCCCATTTACTCAC

E  A  L  H  N  H  Y  T  Q  K  S  L  S  L  S  P  G  K  *

CXH
          FMA
          RAE
          133
           /
      CGACGGCCG
2581  --------- 2589
      GCTGCCGGC
```

TABLE 3

```
                     F N                                S              B
                     N S         B    M    H           DHA             S
                     U P         B    N    G          RAU              T
                     4 B         V    L    A          AE9              X
                     H 2         1    1    1          236              1
                                                       /
      GCCTGTTTGAGAAGCAGCGGGCAAGAAAGACGCAAGCCCAGAGGCCCTGCCATTTCTGTG
   1  ---------+---------+---------+---------+---------+---------+ 60
      CGGACAAACTCTTCGTCGCCCGTTCTTTCTGCGTTCGGGTCTCCGGGACGGTAAAGACAC

B    PS             S                                         S
         DBS  ADNPA       D   DHNA                M       HM           HNC
         DAP  VRLUU       D   RALU                N       AN           PCR
         EN1  AAAM9       E   AEA9                L       EL           AIF
         122  22416       1   2346                1       31           211
          /    / //       /    /                                         /
      GGCTCAGGTCCCTACTGGCTCAGGCCCCTGCCTCCCTCGGCAAGGCCACAATGAACCGGG
  61  ---------+---------+---------+---------+---------+---------+ 120
      CCGAGTCCAGGGATGACCGAGTCCGGGGACGGAGGGAGCCGTTCCGGTGTTACTTGGCCC

M  N  R  G  -

F                  F
         H                         N             HH   N M     D
         I         B               U             HA   U N     D
         N         B               4             AE   4 L     E
         F         V               H             12   H 1     1
         1         1                                    
      GAGTCCCTTTTAGGCACTTGCTTCTGGTGCTGCAACTGGCGCTCCTCCCAGCAGCCACTC
 121  ---------+---------+---------+---------+---------+---------+ 180
      CTCAGGGAAAATCCGTGAACGAAGACCACGACGTTGACCGCGAGGAGGGTCGTCGGTGAG

V  P  F  R  H  L  L  L  V  L  Q  L  A  L  L  P  A  A  T  Q  -

B   E  E                                      R     A
         B   C  C                                      S     L
         V   0  0                                      A     U
         1   K  K                                      1     1
      AGGGAAAGAAAGTGGTGCTGGGCAAAAAAGGGGATACAGTGGAACTGACCTGTACAGCTT
 181  ---------+---------+---------+---------+---------+---------+ 240
      TCCCTTTCTTTCACCACGACCCGTTTTTTCCCCTATGTCACCTTGACTGGACATGTCGAA

G  K  K  V  V  L  G  K  K  G  D  T  V  E  L  T  C  T  A  S  -

H
                       M    M                            I
                       B    B                            N
                       0    0                            F
```

TABLE 3-continued

```
                  2   2                                     1
         CCCAGAAGAAGAGCATACAATTCCACTGGAAAAACTCCAACCAGATAAAGATTCTGGGAA
     241 ---------+---------+---------+---------+---------+---------+ 300
         GGGTCTTCTTCTCGTATGTTAAGGTGACCTTTTTGAGGTTGGTCTATTTCTAAGACCCTT

Q   K  K   S   I   Q   F   H   W   K   N   S   N   Q   I   K   I   L   G   N -

B                       S                   S     F       H
                  N B S             F        A A           A     A     N H     I
                  L A P             0        V U           L     U     U H     N
                  A N 1             K        A 9           U     3     D A     F
                  4 2 2             1        2 6           1     A     2 1     1
                    /                        /
         ATCAGGGCTCCTTCTTAACTAAAGGTCCATCCAAGCTGAATGATCGCGCTGACTCAAGAA
     301 ---------+---------+---------+---------+---------+---------+ 360
         TAGTCCCGAGGAAGAATTGATTTCCAGGTAGGTTCGACTTACTAGCGCGACTGAGTTCTT

Q   G   S   F   L   T   K   G   P   S   K   L   N   D   R   A   D   S   R   R -

S                           S           H                   H
                M A N A S                     B A           I       A           I  D
                B V L U T                     C U           N       F           N  D
                0 A A 9 Y                     L 3           F       L           F  E
                2 2 4 6 1                     1 A           1       2           1  1
                    /                           /
         GAAGCCTTTGGGACCAAGGAAACTTCCCCCTGATCATCAAGAATCTTAAGATAGAAGACT
     361 ---------+---------+---------+---------+---------+---------+ 420
         CTTCGGAAACCCTGGTTCCTTTGAAGGGGGACTAGTAGTTCTTAGAATTCTATCTTCTGA

S   L   W   D   Q   G   N   F   P   L   I   I   K   N   L   K   I   E   D   S -

S
                  M          M                A M A M                       M
                  B          N                V N U N                       A
                  0          L                A L 9 L                       E
                  2          1                2 1 6 1                       1
                                                //
         CAGATACTTACATCTGTGAAGTGGAGGACCAGAAGGAGGAGGTGCAATTGCTAGTGTTCG
     421 ---------+---------+---------+---------+---------+---------+ 480
         GTCTATGAATGTAGACACTTCACCTCCTGGTCTTCCTCCTCCACGTTAACGATCACAAGC

D   T   Y   I   C   E   V   E   D   Q   K   E   E   V   Q   L   L   V   F   G -

B
                                                S
                                                P                               S
                                                M                               T
                                                1                               Y  1
         GATTGACTGCCAACTCTGACACCCACCTGCTTCAGGGGCAGAGCCTGACCCTGACCTTGG
     481 ---------+---------+---------+---------+---------+---------+ 540
         CTAACTGACGGTTGAGACTGTGGGTGGACGAAGTCCCCGTCTCGGACTGGGACTGGAACC

L   T   A   N   S   D   T   H   L   L   Q   G   Q   S   L   T   L   T   L   E -

B        B S                             H
                 B S        S C             D           M   I       S
                 A P        T R             D           N   N       T
                 N 1        N F             E           L   F       Y
                 2 2        1 1             1           1   1       1
                   /        /
         AGAGCCCCCCTGGTAGTAGCCCCTCAGTGCAATGTAGGAGTCCAAGGGGTAAAAACATAC
     541 ---------+---------+---------+---------+---------+---------+ 600
         TCTCGGGGGGACCATCATCGGGGAGTCACGTTACATCCTCAGGTTCCCCATTTTTGTATG

S   P   P   G   S   S   P   S   V   Q   C   R   S   P   R   G   K   N   I   Q -

N            B B H   S     B           B S
                              M       M D      A S P       A B S S G S C   S   B N     S C
                              B       N D      L P V       L A P T I A R   T   A L     T R
                              0       L E      U B U       U N 1 N A C F   X   N A     N F
                              2       1 1      1 2 2       1 2 2 1 1 1 1   1   1 4     1 1
                                                //             / / / /         /
         AGGGGGGGAAGACCCTCTCCGTGTCTCAGCTGGAGCTCCAGGATAGTGGCACCTGGACAT
     601 ---------+---------+---------+---------+---------+---------+ 660
         TCCCCCCCTTCTGGGAGAGGCACAGAGTCGACCTCGAGGTCCTATCACCGTGGACCTGTA

G   G   K   T   L   S   V   S   Q   L   E   L   Q   D   S   G   T   W   T   C -

N
```

TABLE 3-continued

```
      NS                    M              NM   A
      LP                    B              HA   L
      AH                    0              EE   U
      31                    2              11   1
      /
      GCACTGTCTTGCAGAACCAGAAGAAGGTGGAGTTCAAAATAGACATCGTGGTGCTAGCTT
  661 ---------+---------+---------+---------+---------+---------+ 720
      CGTGACAGAACGTCTTGGTCTTCTTCCACCTCAAGTTTTATCTGTAGCACCACGATCGAA

T  V  L  Q  N  Q  K  K  V  E  F  K  I  D  I  V  V  L  A  F-

HS            M  M
             AT            N  N
             EU            L  L
             31            1  1
             /
      TCCAGAAGGCCTCCAGCATAGTCTATAAGAAAGAGGGGGAACAGGTGGAGTTCTCCTTCC
  721 ---------+---------+---------+---------+---------+---------+ 780
      AGGTCTTCCGGAGGTCGTATCAGATATTCTTTCTCCCCTTGTCCACCTCAAGAGGAAGG

Q  K  A  S  S  I  V  Y  K  K  E  G  E  Q  V  E  F  S  F  P-

A              A         M
                           L              L         N
                           U              U         L
                           1              1         1
      CACTCGCCTTTACAGTTGAAAAGCTGACGGGCAGTGGCGAGCTGTGGTGGCAGGCGGAGA
  781 ---------+---------+---------+---------+---------+---------+ 840
      GTGAGCGGAAATGTCAACTTTTCGACTGCCCGTCACCGCTCGACACCACCGTCCGCCTCT

L  A  F  T  V  E  K  L  T  G  S  G  E  L  W  W  Q  A  E  R-

P  S
            H  M FM  A                                   M
            P  N LN  U                                   B
            H  L ML  3                                   0
            1  1 11  A                                   2
      GGGCTTCCTCCTCCAAGTCTTGGATCACCTTTGACCTGAAGAACAAGGAAGTGTCTGTAA
  841 ---------+---------+---------+---------+---------+---------+ 900
      CCCGAAGGAGGAGGTTCAGAACCTAGTGGAAACTGGACTTCTTGTTCCTTCACAGACATT

A  S  S  S  K  S  W  I  T  F  D  L  K  N  K  E  V  S  V  K-

B         BS  PS
          SM        SCADNPAD      A             A  H
          TA        TRVRLUUD      L             L  P
          EE        NFAAAM9E      U             U  H
          23        11224161      1             1  1
                    /      / / //
      AACGGGTTACCCAGGACCCTAAGCTCCAGATGGGCAAGAAGCTCCCGCTCCACCTCACCC
  901 ---------+---------+---------+---------+---------+---------+ 960
      TTGCCCAATGGGTCCTGGGATTCGAGGTCTACCCGTTCTTCGAGGGCGAGGTGGAGTGGG

R  V  T  Q  D  P  K  L  Q  M  G  K  K  L  P  L  H  L  T  L-

BS                                  BSS
       M   SC HS     D          M   H              SCAHM
       N   TR AT     D          N   P              TRUAN
       L   NF EU     E          L   H              NF9EL
       1   11 31     1          1   1              11631
                /                                  /  /
      TGCCCCAGGCCTTGCCTCAGTATGCTGGCTCTGGAAACCTCACCCTGGCCCTTGAAGCGA
  961 ---------+---------+---------+---------+---------+---------+ 1020
      ACGGGGTCCGGAACGGAGTCATACGACCGAGACCTTTGGAGTGGGACCGGGAACTTCGCT

P  Q  A  L  P  Q  Y  A  G  S  G  N  L  T  L  A  L  E  A  K-

S       BS
                        F       SC            H  D        A
                        A       TR            P  D        L
                        N       NF            H  E        U
                        1       11            1  1        1
                                                /
      AAACAGGAAAGTTGCATCAGGAAGTGAACCTGGTGGTGATGAGAGCCACTCAGCTCCAGA
 1021 ---------+---------+---------+---------+---------+---------+ 1080
      TTTGTCCTTTCAACGTAGTCCTTCACTTGGACCACCACTACTCTCGGTGAGTCGAGGTCT

T  G  K  L  H  Q  E  V  N  L  V  V  M  R  A  T  Q  L  Q  K-
```

TABLE 3-continued

```
                            PS          S
       M                    ADNNPA      DF    AM    DE    A
       N                    VRLLUU      DA    LN    DS    L
       L                    AAAAM9      EN    UL    EP    U
       1                    224416      11    11    11    1
                            /////       /     /     /
     AAAATTTGACCTGTGAGGTGTGGGGACCCACCTCCCCTAAGCTGATGCTGAGCTTGAAAC
1081 ---------+---------+---------+---------+---------+---------+ 1140
     TTTTAAACTGGACACTCCACACCCCTGGGTGGAGGGGATTCGACTACGACTCGAACTTTG

N    L    T    C    E    V    W    G    P    T    S    P    K    L    M    L    S    L    K    L  -

M                        T                   H              M              DM
       N                        A                   P              N              DS
       L                        Q                   A              L              ET
                                                                                  /
     TGGAGAACAAGGAGGCAAAGGTCTCGAAGCGGGAGAAGCCGGTGTGGGTGCTGAACCCTG
1141 ---------+---------+---------+---------+---------+---------+ 1200
     ACCTCTTGTTCCTCCGTTTCCAGAGCTTCGCCCTCTTCGGCCACACCCACGACTTGGGAC

E    N    K    E    A    K    V    S    K    R    E    K    P    V    W    V    L    N    P    E  -

H                         PS         H
                    F    D    M    I    A                     ADPA       I
                    0    D    A    N    V                     VRUU       N
                    K    E    E    F    A                     AAM9       F
                    1    1    3    1    1                     2216       1
                                                              ///
     AGGCGGGGATGTGGCAGTGTCTGCTGAGTGACTCGGGACAGGTCCTGCTGGAATCCAACA
1201 ---------+---------+---------+---------+---------+---------+ 1260
     TCCGCCCCTACACCGTCACAGACGACTCACTGAGCCCTGTCCAGGACGACCTTAGGTTGT

A    G    M    W    Q    C    L    L    S    D    S    G    Q    V    L    L    E    S    N    I  -

S         SA      BHF BS                   H
                              ANA       HNCP    SGNMAANXA        RSD  I  A
                              VLU       PCRA    PIUNMALHV        SCD  N  L
                              AA9       AIFL    1ADLH3A0A        AAE  D  U
                              236       2111    21211A421        111  3  1
                              //        //      / / / /
     TCAAGGTTCTGCCCACATGGTCCACCCCGGTGCACGCGGATCCCGAGGGTGAGTACTAAG
1261 ---------+---------+---------+---------+---------+---------+ 1320
     AGTTCCAAGACGGGTGTACCAGGTGGGGCCACGTGCGCCTAGGGCTCCCACTCATGATTC

K    V    L    P    T    W    S    T    P    V    H    A    D    P    E

E              BS              SS           F              BS      F
            H       CHH    F       SC              HHNCF        N              BSC     N
            P       0HA    0       TR              PGCRA        U              BTR     U
            H       4AE    K       NF              AAIFN        4              VNF     4
            1       712    1       11              21111        H              111     H
            /              //                      / /                         //
     CTTCAGCGCTCCTGCCTGGACGCATCCCGGCTATGCAGCCCCAGTCCAGGGCAGCAAGGC
1321 ---------+---------+---------+---------+---------+---------+ 1380
     GAAGTCGCGAGGACGGACCTGCGTAGGGCCGATACGTCGGGGTCAGGTCCCGTCGTTCCG

S                      S
       DBHMHNA                 HMNCN              M              MNDM
       RBABPLU                 PNCRL              N              NLDB
       AVE0HA9                 ALIFA              L              LAE0
       2132146                 21114              1              1312
       // //                   //
     AGGCCCCGTCTGCCTCTTCACCCGGAGCCTCTGCCCGCCCCACTCATGCTCAGGGAGAGG
1381 ---------+---------+---------+---------+---------+---------+ 1440
     TCCGGGGCAGACGGAGAAGTGGGCCTCGGAGACGGGCGGGGTGAGTACGAGTCCCTCTCC

BS    P                       B             BS    S
                             SC    F              M   B  N  S            SCDHA
                             TR    L              A   A  L  P            TRRAU
                             NF    M              E   N  A  1            NFAE9
                             11    1              1   1  4  2            11236
                             /                                           / /
     GTCTTCTGGCTTTTTCCCAGGCTCTGGGCAGGCACAGGCTAGGTGCCCTAACCCAGGCC
1441 ---------+---------+---------+---------+---------+---------+ 1500
     CAGAAGACCGAAAAAGGGTCCGAGACCCGTCCGTGTCCGATCCACGGGGATTGGGTCCGG

B                     B              B           S        PS
                 S                     DBS            S    M      HNC      ADNPA
                 P                     DAP            P    N      PCR      VRLUU
```

TABLE 3-continued

```
              M            EN1         M    L     AIF   AAAM9
              1            122         1    1     211   22416
                                                  /     / //
     CTGCACACAAAGGGGCAGGTGCTGGGCTCAGACCTGCCAAGAGCCATATCCGGGAGGACC
1501 ---------+---------+---------+---------+---------+---------+ 1560
     GACGTGTGTTTCCCCGTCCACGACCCGAGTCTGGACGGTTCTCGGTATAGGCCCTCCTGG

D            H                D  A     M
              D            A                D  L     N
              E            E                E  U     L
              1            3                1  1     1
     CTGCCCCTGACCTAAGCCCACCCCAAAGGCCAAACTCTCCACTCCCTCAGCTCGGACACC
1561 ---------+---------+---------+---------+---------+---------+ 1620
     GACGGGGACTGGATTCGGGTGGGGTTTCCGGTTTGAGAGGTGAGGGAGTCGAGCCTGTGG

L  P  L  T  *  A  H  P  K  G  Q  T  L  H  S  L  S  S  D  T  -
     C  P  *  P  K  P  T  P  K  A  K  L  S  T  P  S  A  R  T  P  -
     A  P  D  L  S  P  P  Q  R  P  N  S  P  L  P  Q  L  G  H  L  -

H                                          S
           I    M    MM                   DF                    F
           N    N    AB                   D0                    A
           F    L    E0                   EK                    N
           1    1    32                   11                    1
                     /                    /
     TTCTCTCCTCCCAGATTCCAGTAACTCCCAATCTTCTCTCTCAGGGAGTGCATCCGCCCC
1621 ---------+---------+---------+---------+---------+---------+ 1680
     AAGAGAGGAGGGTCTAAGGTCATTGAGGGTTAGAAGAGAGAGTCCCTCACGTAGGCGGGG

G  S  A  S  A  P  -

E
                    M      C
                    N      0
                    L      R
                    1      1
     AACCCTTTTCCCCCTCGTCTCCTGTGAGAATTCC....
1681 ---------+---------+---------+----     1714
     TTGGGAAAAGGGGGAGCAGAGGACACTCTTAAGG....

T  L  F  P  L  V  S  C  E  N  S  ....
```

TABLE 4

```
              F  N
              N  S              S                              B
              U  P     B    M   H   DHA                        S
              4  B     B    N   G   RAU                        T
              H  2     V    L   A   AE9                        X
                       1    1   1   236                        1
                                    /
     GCCTGTTTGAGAAGCAGCGGGCAAGAAAGACGCAAGCCCAGAGGCCCTGCCATTTCTGTG
1    ----------+----------+----------+----------+----------+----------+ 60
     CGGACAAACTCTTCGTCGCCCGTTCTTTCTGCGTTCGGGTCTCCGGGACGGTAAAGACAC

B     PS          S
        DBS   ADNPA     D    DHNA          M    HM         HNC
        DAP   VRLUU     D    RALU          N    AN         PCR
        EN1   AAAM9     E    AEA9          L    EL         AIF
        122   22416     1    2346          1    31         211
         /    / //           /                             /
     GGCTCAGGTCCCTACTGGCTCAGGCCCCTGCCTCCCTCGGCAAGGCCACAATGAACCGGG
61   ----------+----------+----------+----------+----------+----------+ 120
     CCGAGTCCAGGGATGACCGAGTCCGGGGACGGAGGGAGCCGTTCCGGTGTTACTTGGCCC

M  N  R  G  -

F
           H                            N                F
           I          B            HH   U    HH          N  M   D
           N          B       4    HA   4    AE          U  N   D
           F          V       H    12   H    12          4  L   E
           1          1            12                    H  1   1
     GAGTCCCTTTTAGGCACTTGCTTCTGGTGCTGCAACTGGCGCTCCTCCCAGCAGCCACTC
121  ----------+----------+----------+----------+----------+----------+ 180
     CTCAGGGAAAATCCGTGAACGAAGACCACGACGTTGACCGCGAGGAGGGTCGTCGGTGAG

V  P  F  R  H  L  L  L  V  L  Q  L  A  L  L  P  A  A  T  Q  -
```

TABLE 4-continued

```
       B      E   E                                                R    A
       B      C   C                                                S    L
       V      O   O                                                A    U
       1      K   K                                                1    1
     AGGGAAAGAAAGTGGTGCTGGGCAAAAAAGGGGATACAGTGGAACTGACCTGTACAGCTT
181  ----------+----------+----------+----------+----------+----------+ 240
     TCCCTTTCTTTCACCACGACCCGTTTTTTCCCCTATGTCACCTTGACTGGACATGTCGAA

G    K   K    V    V    L    G    K    K    G    D    T    V    E    L    T    C    T    A    S  -

H
                   M   M                                                I
                   B   B                                                N
                   0   0                                                F
                   2   2                                                1
     CCCAGAAGAAGAGCATACAATTCCACTGGAAAAACTCCAACCAGATAAAGATTCTGGGAA
241  ----------+----------+----------+----------+----------+----------+ 300
     GGGTCTTCTTCTCGTATGTTAAGGTGACCTTTTTGAGGTTGGTCTATTTCTAAGACCCTT

Q    K    K    S    I    Q    F    H    W    K    N    S    N    Q    I    K    I    L    G    N  -

B                      S                   S    F    H
            NBS          F          AA         A       A    N    I
            LAP          O          VU         L       U    H    N
            AN1          K          A9         U       3    D    A F
            422          1          26         1       A    2    1 1
                                    /                       /
     ATCAGGGCTCCTTCTTAACTAAAGGTCCATCCAAGCTGAATGATCGCGCTGACTCAAGAA
301  ----------+----------+----------+----------+----------+----------+ 360
     TAGTCCCGAGGAAGAATTGATTTCCAGGTAGGTTCGACTTACTAGCGCGACTGAGTTCTT
     Q  G    S    F    L    T    K    G    P    S    K    L    N    D    R    A    D    S    R    R

S                  S                    H                 H
                 MANAS                    BA           I    A                   I    D
                 BVLUT                    CU           N    F                   N    D
                 0AA9Y                    L3           F    L                   F    E
                 22461                    1A           1    2                   1    1
                   /                        /
     GAAGCCTTTGGGACCAAGGAAACTTCCCCCTGATCATCAAGAATCTTAAGATAGAAGACT
361  ----------+----------+----------+----------+----------+----------+ 420
     CTTCGGAAACCCTGGTTCCTTTGAAGGGGGACTAGTAGTTCTTAGAATTCTATCTTCTGA

S    L    W    D    Q    G    N    F    P    L    I    I    K    N    L    K    I    E    D    S  -

S
           M               M              AMAM                       M
           B               N              VNUN                       A
           0               L              AL9L                       E
           2               1              2161                       1
                                           //
     CAGATACTTACATCTGTGAAGTGGAGGACCAGAAGGAGGAGGTGCAATTGCTAGTGTTCG
421  ----------+----------+----------+----------+----------+----------+ 480
     GTCTATGAATGTAGACACTTCACCTCCTGGTCTTCCTCCTCCACGTTAACGATCACAAGC

D    T    Y    I    C    E    V    E    D    Q    K    E    E    V    Q    L    L    V    F    G  -

B
                                                   S                                        S
                                                   P                                        T
                                                   M                                        Y
                                                   1                                        1
     GATTGACTGCCAACTCTGACACCCACCTGCTTCAGGGGCAGAGCCTGACCCTGACCTTGG
481  ----------+----------+----------+----------+----------+----------+ 540
     CTAACTGACGGTTGAGACTGTGGGTGGACGAAGTCCCCGTCTCGGACTGGGACTGGAACC
         L    T    A    N    S    D    T    H    L    L    Q    G    Q    S    L    T    L    T    L    E

B    BS                                H
            BS   SC             D             M    I    S
            AP   TR             D             N    N    T
            N1   NF             E             L    F    Y
            22   11             1             1    1    1
             /    /
     AGAGCCCCCCTGGTAGTAGCCCCTCAGTGCAATGTAGGAGTCCAAGGGGTAAAAACATAC
541  ----------+----------+----------+----------+----------+----------+ 600
     TCTCGGGGGGACCATCATCGGGGAGTCACGTTACATCCTCAGGTTCCCCATTTTTGTATG
         S    P    P    G    S    S    P    S    V    Q    C    R    S    P    R    G    K    N    I    Q  -

N        BBH S   B           BS
```

TABLE 4-continued

```
                        M   MD   ASP    A  BSSGSC   S   B  N   SC
                        B   ND   LPV    L  APTIAR   T   A  L   TR
                        0   LE   UBU    U  N1NACF   X   N  A   NF
                        2   11   122    1  221111   1   1  4   11
                             //      /  ///             /
     AGGGGGGGAAGACCCTCTCCGTGTCTCAGCTGGAGCTCCAGGATAGTGGCACCTGGACAT
601  ----------+----------+----------+----------+----------+----------+ 660
     TCCCCCCCTTCTGGGAGAGGCACAGAGTCGACCTCGAGGTCCTATCACCGTGGACCTGTA
       G  G  K  T  L  S  V  S  Q  L  E  L  Q  D  S  G  T  W  T  C  -

N
              NS                       M                    NM    A
              LP                       B                    HA    L
              AH                       0                    EE    U
              31                       2                    11    1
               /
     GCACTGTCTTGCAGAACCAGAAGAAGGTGGAGTTCAAAATAGACATCGTGGTGCTAGCTT
661  ----------+----------+----------+----------+----------+----------+ 720
     CGTGACAGAACGTCTTGGTCTTCTTCCACCTCAAGTTTTATCTGTAGCACCACGATCGAA
       T  V  L  Q  N  Q  K  K  V  E  F  K  I  D  I  V  V  L  A  F  -

HS       M  M
              AT       N  N
              EU       L  L
              31       1  1
               /
     TCCAGAAGGCCTCCAGCATAGTCTATAAGAAAGAGGGGGAACAGGTGGAGTTCTCCTTCC
721  ----------+----------+----------+----------+----------+----------+ 780
     AGGTCTTCCGGAGGTCGTATCAGATATTCTTTCTCCCCCTTGTCCACCTCAAGAGGAAGG
       Q  K  A  S  S  I  V  Y  K  K  E  G  E  Q  V  E  F  S  F  P  -

A              A         M
                          L              L         N
                          U              U         L
                          1              1         1
     CACTCGCCTTTACAGTTGAAAAGCTGACGGGCAGTGGCGAGCTGTGGTGGCAGGCGGAGA
781  ----------+----------+----------+----------+----------+----------+ 840
     GTGAGCGGAAATGTCAACTTTTCGACTGCCCGTCACCGCTCGACACCACCGTCCGCCTCT
       L  A  F  T  V  E  K  L  T  G  S  G  E  L  W  W  Q  A  E  R  -

P  S
              H     M  FM A                              M
              P     N  LN U                              B
              H     L  ML 3                              0
              1     1  11 A                              2
     GGGCTTCCTCCTCCAAGTCTTGGATCACCTTTGACCTGAAGAACAAGGAAGTGTCTGTAA
841  ----------+----------+----------+----------+----------+----------+ 900
     CCCGAAGGAGGAGGTTCAGAACCTAGTGGAAACTGGACTTCTTGTTCCTTCACAGACATT
       A  S  S  S  K  S  W  I  T  F  D  L  K  N  K  E  V  S  V  K  -

B      BS   PS
              SM     SCADNPAD    A              A  H
              TA     TRVRLUUD    L              L  P
              EE     NFAAAM9E    U              U  H
              23     11224161    1              1  1
               /      / / //
     AACGGGTTACCCAGGACCCTAAGCTCCAGATGGGCAAGAAGCTCCCGCTCCACCTCACCC
901  ----------+----------+----------+----------+----------+----------+ 960
     TTGCCCAATGGGTCCTGGGATTCGAGGTCTACCCGTTCTTCGAGGGCGAGGTGGAGTGGG
       R  V  T  Q  D  P  K  L  Q  M  G  K  K  L  P  L  H  L  T  L  -

BS                                  BSS
       M    SC HS      D          M  H              SCAHM
       N    TR AT      D          N  P              TRUAN
       L    NF EU      E          L  H              NF9EL
       1    11 31      1          1  1              11631
             /  /                                    / /
     TGCCCCAGGCCTTGCCTCAGTATGCTGGCTCTGGAAACCTCACCCTGGCCCTTGAAGCGA
961  ----------+----------+----------+----------+----------+----------+ 1020
     ACGGGGTCCGGAACGGAGTCATACGACCGAGACCTTTGGAGTGGGACCGGGAACTTCGCT
       P  Q  A  L  P  Q  Y  A  G  S  N  L  T  L  A  L  E  A  K  -

S       BS
                      F       SC               H  D     A
                      A       TR               P  D     L
                      N       NF               H  E     U
                      1       11               1  1     1
                               /
```

TABLE 4-continued

```
     AAACAGGAAAGTTGCATCAGGAAGTGAACCTGGTGGTGATGAGAGCCACTCAGCTCCAGA
1021 ----------+----------+----------+----------+----------+----------+ 1080
     TTTGTCCTTTCAACGTAGTCCTTCACTTGGACCACCACTACTCTCGGTGAGTCGAGGTCT

T  G  K  L  H  Q  E  V  N  L  V  V  M  R  A  T  Q  L  Q  K -

PS           S
           M          ADNNPA        DF      AM       DE     A
           N          VRLLUU        DA      LN       DS     L
           L          AAAAM9        EN      UL       EP     U
           1          224416        11      11       11     1
                      /////          /       /        /
     AAAATTTGACCTGTGAGGTGTGGGGACCCACCTCCCCTAAGCTGATGCTGAGCTTGAAAC
1081 ----------+----------+----------+----------+----------+----------+ 1140
     TTTTAAACTGGACACTCCACACCCCTGGGTGGAGGGGATTCGACTACGACTCGAACTTTG

N  L  T  C  E  V  W  G  P  T  S  P  K  L  M  L  S  L  K  L -

M                T              H           M        DM
           N                A              P           N        DS
           L                Q              A           L        ET
           1                1              2           1        12
                                                                /
     TGGAGAACAAGGAGGCAAAGGTCTCGAAGCGGGAGAAGCCGGTGTGGGTGCTGAACCCTG
1141 ----------+----------+----------+----------+----------+----------+ 1200
     ACCTCTTGTTCCTCCGTTTCCAGAGCTTCGCCCTCTTCGGCCACACCCACGACTTGGGAC

E  N  K  E  A  K  V  S  R  E  K  P  V  W  V  L  N  P  E -

H                PS         H
                 F    D   M   I A            ADPA           I
                 0    D   A   N V            VRUU           N
                 K    E   E   F A            AAM9           F
                 1    1   3   1 1            2216           1
                                                 ///
     AGGCGGGGATGTGGCAGTGTCTGCTGAGTGACTCGGGACAGGTCCTGCTGGAATCCAACA
1201 ----------+----------+----------+----------+----------+----------+ 1260
     TCCGCCCCTACACCGTCACAGACGACTCACTGAGCCCTGTCCAGGACGACCTTAGGTTGT

A  G  M  W  Q  C  L  L  S  D  S  G  Q  B  L  L  E  S  N  I -

S            SA      BHF BS                H
                      ANA          HNCP    SGNMAANXA         RSD I A
                      VLU          PCRA    PIUNMULHV         SCD N L
                      AA9          AIFL    1ADLH3ADA         AAE D U
                      236          2111    21211A421         111 3 1
                      //            //     ////               /
     TCAAGGTTCTGCCCACATGGTCCACCCCGGTGCACGCGGATCCCGAGGGTGAGTACTAAG
1261 ----------+----------+----------+----------+----------+----------+ 1320
     AGTTCCAAGACGGGTGTACCAGGTGGGGCCACGTGCGCCTAGGGCTCCCACTCATGATTC

K  V  L  P  T  W  S  T  P  V  H  A  D  P  E

E        BS              SS      F            BS   F
           H     CHH   F   SC            HHNCF    N           BSC   N
           P     0HA   0   TR            PGCRA    U           BTR   U
           H     4AE   K   NF            AAIFN    4           VNF   4
           1     712   1   11            21111    H           111   H
                 /         /             //                  //
     CTTCAGCGCTCCTGCCTGGACGCATCCCGGCTATGCAGCCCCAGTCCAGGGCAGCAAGGC
1321 ----------+----------+----------+----------+----------+----------+ 1380
     GAAGTCGCGAGGACGGACCTGCGTAGGGCCGATACGTCGGGGTCAGGTCCCGTCGTTCCG

S                       S
           DBHMHNA              HMNCN              M          MNDM
           RBABPLU              PNCRL              N          NLDB
           AVE0HA9              ALIFA              L          LAE0
           2132146              21114              1          1312
            // //                //
     AGGCCCCGTCTGCCTCTTCACCCGGAGCCTCTGCCCGCCCCACTCATGCTCAGGGAGAGG
1381 ----------+----------+----------+----------+----------+----------+ 1440
     TCCGGGGCAGACGGAGAAGTGGGCCTCGGAGACGGGCGGGGTGAGTACGAGTCCCTCTCC

BS    P                       B       BS   S
                      SC    F              M   B N  S       SCDHA
                      TR    L              A   A L  P       TRRAU
                      NF    M              E   N A  1       NFAE9
                      11    1              1   1 4  2       11236
                      /                                      / /
     GTCTTCTGGCTTTTTCCCAGGCTCTGGGCAGGCACAGGCTAGGTGCCCCTAACCCAGGCC
1441 ----------+----------+----------+----------+----------+----------+ 1500
     CAGAAGACCGAAAAAGGGTCCGAGACCCGTCCGTGTCCGATCCACGGGGATTGGGTCCGG
```

TABLE 4-continued

```
                 B              B        B          S       PS
         S       DBS            S    M   HNC       ADNPA
         P       DAP            P    N   PCR       VRLUU
         M       EN1            M    L   AIF       AAAM9
         1       122            1    1   211       22416
                   /                      /        / //
     CTGCACACAAAGGGGCAGGTGCTGGGCTCAGACCTGCCAAGAGCCATATCCGGGAGGACC
1501 ----------+----------+----------+----------+----------+----------+ 1560
     GACGTGTGTTTCCCCGTCCACGACCCGAGTCTGGACGGTTCTCGGTATAGGCCCTCCTGG

D              H              D    A    M
                 D              A              D    L    N
                 E              E              E    U    L
                 1              3              1    1    1
     CTGCCCCTGACCTAAGCCCACCCCAAAGGCCAAACTCTCCACTCCCTCAGCTCGGACACC
1561 ----------+----------+----------+----------+----------+----------+ 1620
     GACGGGGACTGGATTCGGGTGGGGTTTCCGGTTTGAGAGGTGAGGGAGTCGAGCCTGTGG

H                                      F
             I    M   MM                     BP     DE      AN
             N    N   AB                     BS     DS      LU
             F    L   ED                     VT     EP      U4
             1    1   32                     11     11      1H
                        /                     /      /
     TTCTCTCCTCCCAGATTCCAGTAACTCCCAATCTTCTCTCTGCAGTGATTGCTGAGCTGC
1621 ----------+----------+----------+----------+----------+----------+ 1680
     AAGAGAGGAGGGTCTAAGGTCATTGAGGGTTAGAAGAGAGACGTCACTAACGACTCGACG

V  I  A  E  L  P  -

F
         M H   M              M  N
         B G   N              B  U
         D A   L              D  D
         2 1   1              2  2
     CTCCCAAAGTGAGCGTCTTCGTCCCACCCCGCGACGGCTTCTTCGGCAACCCCCGCAAGT
1681 ----------+----------+----------+----------+----------+----------+ 1740
     GAGGGTTTCACTCGCAGAAGCAGGGTGGGGCGCTGCCGAAGAAGCCGTTGGGGGCGTTCA

P   K    V    S    V    F    V    P    P    R    D    G    F    F    G    C    P    R    K    S    -

BS             S     H              B S F
         A      SC  H         HNC   I  B           SMC N
         L      TR  A         PCR   N  B           TNR U
         U      NF  E         AIF   F  V           NLF 4
         1      11  3         211   1  1           111 H
                  /             //                  /
     CCAAGCTCATCTGCCAGGCCACGGGTTTCAGTCCCCGGCAGATTCAGGTGTCCTGGCTGC
1741 ----------+----------+----------+----------+----------+----------+ 1800
     GGTTCGAGTAGACGGTCCGGTGCCCAAAGTCAGGGGCCGTCTAAGTCCACAGGACCGACG

K    L    I    C    Q    A    T    G    F    S    P    R    Q    I    Q    V    S    W    L    R    -

F    B                          S    BS                  H
      NH   S        H  H    AM        AA   SCM      D    H     I
      UH   P        P  G    HA        VU   TRN      D    A     N
      DA   M        H  A    AE        A9   NFL      E    E     F
      21   1        1  1    23        26   111      1    3     1
       /                                    / /
     GCGAGGGGAAGCAGGTGGGGTCTGGCGTCACCACGGACCAGGTGCAGGCTGAGGCCAAAG
1801 ----------+----------+----------+----------+----------+----------+ 1860
     CGCTCCCCTTCGTCCACCCCAGACCGCAGTGGTGCCTGGTCCACGTCCGACTCCGGTTTC

E    G    K    Q    V    G    S    G    V    T    T    D    Q    V    Q    A    E    A    K    E    -

SS       B
              AAHNABS          SM               H
              UUALPAP          TA               P
              99EAAN1          EE               H
              6634122          23               1
                / //            /
     AGTCTGGGCCCACGACCTACAAGGTGACCAGCACACTGACCATCAAAGAG...
1861 ----------+----------+----------+----------+----------+ 1910
     TCAGACCCGGGTGCTGGATGTTCCACTGGTCGTGTGACTGGTAGTTTCTC...

S    G    P    T    T    Y    K    V    T    S    T    L    T    I    K    E    ...
```

TABLE 5

```
            F N                         S
            N S       B    M    H       DHA           B
            U P       B    N    G       RAE9          S
            4 B       V    L    A       AE9           T X
            H 2       1    1    1       236           1
                                         /
    GCCTGTTTGAGAAGCAGCGGGCAAGAAAGACGCAAGCCCAGAGGCCCTGCCATTTCTGTG
1   ----------+----------+----------+----------+----------+----------+  60
    CGGACAAACTCTTCGTCGCCCGTTCTTTCTGCGTTCGGGTCTCCGGGACGGTAAAGACAC

B    PS                 S
    DBS  ADNPA       D     DHNA                              S
    DAP  VRLUU       D     RALU             M     HM         HNC
    EN1  AAAM9       E     AEA9             N     AN         PCR
    122  22416       1     2346             L     EL         AIF
     /    / //                 /                   31        211
                                                               /
    GGCTCAGGTCCCTACTGGCTCAGGCCCCTGCCTCCCTCGGCAAGGCCACAATGAACCGGG
61  ----------+----------+----------+----------+----------+----------+  120
    CCGAGTCCAGGGATGACCGAGTCCGGGGACGGAGGGAGCCGTTCCGGTGTTACTTGGCCC

M  N  R  G -

H                       F                    F
    I              B        N         HH         N  M         D
    N              B        U         HA         U  N         D
    F              V        4         AE         4  L         E
    1              1        H         12         H  1         1
    GAGTCCCTTTTAGGCACTTGCTTCTGGTGCTGCAACTGGCGCTCCTCCCAGCAGCCACTC
121 ----------+----------+----------+----------+----------+----------+  180
    CTCAGGGAAAATCCGTGAACGAAGACCACGACGTTGACCGCGAGGAGGGTCGTCGGTGAG

V  P  F  R  H  L  L  V  L  Q  L  A  L  L  P  A  A  T  Q -

B         E  E                                       R   A
         B         C  C                                       S   L
         V         0  0                                       A   U
         1         K  K                                       1   1
    AGGGAAAGAAAGTGGTGCTGGGCAAAAAAGGGGATACAGTGGAACTGACCTGTACAGCTT
181 ----------+----------+----------+----------+----------+----------+  240
    TCCCTTTCTTTCACCACGACCCGTTTTTTCCCTATGTCACCTTGACTGGACATGTCGAA

G  K  K  V  V  L  G  K  K  G  D  T  V  E  L  T  C  T  A  S -

H
                          M  M                            I
                          B  B                            N
                          0  0                            F
                          2  2                            1
    CCCAGAAGAAGAGCATACAATTCCACTGGAAAAACTCCAACCAGATAAAGATTCTGGGAA
241 ----------+----------+----------+----------+----------+----------+  300
    GGGTCTTCTTCTCGTATGTTAAGGTGACCTTTTTGAGGTTGGTCTATTTCTAAGACCCTT

Q  K  K  S  I  Q  F  H  W  K  N  S  N  Q  I  K  I  L  G  N -

B                S                  S   F     H
                      NBS           F    AA           A     A   NH    I
                      LAP           0    VU           L     U   UH    N
                      AN1           K    A9           U     3   DA    F
                      422           1    26           1     A   21    1
                       /                  /
    ATCAGGGCTCCTTCTTAACTAAAGGTCCATCCAAGCTGAATGATCGCGCTGACTCAAGAA
301 ----------+----------+----------+----------+----------+----------+  360
    TAGTCCCGAGGAAGAATTGATTTCCAGGTAGGTTCGACTTACTAGCGCGACTGAGTTCTT

Q  G  S  F  L  T  K  G  P  S  K  L  N  D  R  A  D  S  R  R -

S                      S           H               H
            MANAS                      BA          I    A          I D
            BVLUT                      CU          N    F          N D
            0AA9Y                      L3          F    L          F E
            22461                      1A          1    2          1 1
              /                         /
    GAAGCCTTTGGGACCAAGGAAACTTCCCCCTGATCATCAAGAATCTTAAGATAGAAGACT
361 ----------+----------+----------+----------+----------+----------+  420
    CTTCGGAAACCCTGGTTCCTTTGAAGGGGGACTAGTAGTTCTTAGAATTCTATCTTCTGA

S  L  W  D  Q  G  N  F  P  L  I  I  K  N  L  K  I  E  D  S -
                                                                  S
```

TABLE 5-continued

```
              M       M              AMAM                      M
              B       N              VNUN                      A
              0       L              AL9L                      E
              2       1              2161                      1
                                      //
     CAGATACTTACATCTGTGAAGTGGAGGACCAGAAGGAGGAGGTGCAATTGCTAGTGTTCG
421  ----------+----------+----------+----------+----------+----------+ 480
     GTCTATGAATGTAGACACTTCACCTCCTGGTCTTCCTCCTCCACGTTAACGATCACAAGC

D  T  Y  I  C  E  V  E  D  Q  K  E  E  V  Q  L  L  V  F  G  -

B
                                     S
                                     P                         S
                                     M                         T
                                     1                         Y
                                                               1
     GATTGACTGCCAACTCTGACACCCACCTGCTTCAGGGGCAGAGCCTGACCCTGACCTTGG
481  ----------+----------+----------+----------+----------+----------+ 540
     CTAACTGACGGTTGAGACTGTGGGTGGACGAAGTCCCCGTCTCGGACTGGGACTGGAACC

L  T  A  N  S  D  T  H  L  L  Q  G  Q  S  L  T  L  T  L  E  -

B   BS                                   H
         BS  SC              D         M          I       S
         AP  TR              D         N          N       T
         N1  NF              E         L          F       Y
         22  11              1         1          1       1
          /  /
     AGAGCCCCCCTGGTAGTAGCCCCTCAGTGCAATGTAGGAGTCCAAGGGGTAAAAACATAC
541  ----------+----------+----------+----------+----------+----------+ 600
     TCTCGGGGGGACCATCATCGGGGAGTCACGTTACATCCTCAGGTTCCCCATTTTTGTATG

S  P  P  G  S  S  P  S  V  Q  C  R  S  P  R  G  K  N  I  Q  -

N         BBH S  B              BS
                   M    MD     ASP     A  BSSGSC  S     B  N    SC
                   B    ND     LPV     L  APTIAR  T     A  L    TR
                   0    LE     UBU     U  N1NACF  X     N  A    NF
                   2    11     122     1  221111  1     1  4    11
                          //              /  ///                /
     AGGGGGGGAAGACCCTCTCCGTGTCTCAGCTGGAGCTCCAGGATAGTGGCACCTGGACAT
601  ----------+----------+----------+----------+----------+----------+ 660
     TCCCCCCCTTCTGGGAGAGGCACAGAGTCGACCTCGAGGTCCTATCACCGTGGACCTGTA

G  G  K  T  L  S  V  S  Q  L  E  L  Q  D  S  G  T  W  T  C  -

N
       NS
       LP                           M                   NM       A
       AH                           B                   HA       L
       31                           0                   EE       U
        /                           2                   11       1
     GCACTGTCTTGCAGAACCAGAAGAAGGTGGAGTTCAAAATAGACATCGTGGTGCTAGCTT
661  ----------+----------+----------+----------+----------+----------+ 720
     CGTGACAGAACGTCTTGGTCTTCTTCCACCTCAAGTTTTATCTGTAGCACCACGATCGAA

T  V  L  Q  N  Q  K  K  V  E  F  K  I  D  I  V  V  L  A  F  -

HS           M  M
                 AT           N  N
                 EU           L  L
                 31           1  1
                  /
     TCCAGAAGGCCTCCAGCATAGTCTATAAGAAAGAGGGGAACAGGTGGAGTTCTCCTTCC
721  ----------+----------+----------+----------+----------+----------+ 780
     AGGTCTTCCGGAGGTCGTATCAGATATTCTTTCTCCCCCTTGTCCACCTCAAGAGGAAGG

Q  K  A  S  S  I  V  Y  K  K  E  G  E  Q  V  E  F  S  F  P  -

A                    A       M
                             L                    L       N
                             U                    U       L
                             1                    1       1
     CACTCGCCTTTACAGTTGAAAAGCTGACGGGCAGTGGCGAGCTGTGGTGGCAGGCGGAGA
781  ----------+----------+----------+----------+----------+----------+ 840
     GTGAGCGGAAATGTCAACTTTTCGACTGCCCGTCACCGCTCGACACCACCGTCCGCCTCT

L  A  F  T  V  E  K  L  T  G  S  G  E  L  W  W  Q  A  E  R  -

P    S
              H     M  FM   A                              M
              P     N  LN   U                              B
              H     L  ML   3                              0
```

TABLE 5-continued

```
              1    1 11  A                      2
         GGGCTTCCTCCTCCAAGTCTTGGATCACCTTTGACCTGAAGAACAAGGAAGTGTCTGTAA
   841   ----------+---------+---------+---------+---------+---------+  900
         CCCGAAGGAGGAGGTTCAGAACCTAGTGGAAACTGGACTTCTTGTTCCTTCACAGACATT

A  S  S  S  K  S  W  I  T  F  D  L  K  N  K  E  V  S  V  K  -

B          BS       PS
             SM         SCADNPAD  A              A  H
             TA         TRVRLUUD  L              L  P
             EE         NFAAAM9E  U              U  H
             23         11224161  1              1  1
              /          ////
         AACGGGTTACCCAGGACCCTAAGCTCCAGATGGGCAAGAAGCTCCCGCTCCACCTCACCC
   901   ----------+---------+---------+---------+---------+---------+  960
         TTGCCCAATGGGTCCTGGGATTCGAGGTCTACCCGTTCTTCGAGGGCGAGGTGGAGTGGG

R  V  T  Q  D  P  K  L  Q  M  G  K  K  L  P  L  H  L  T  L  -

BS                                          BSS
          M    SC HS    D         M  H                       SCAHM
          N    TR AT    D         N  P                       TRUAN
          L    NF EU    E         L  H                       NF9EL
          1    11 31    1         1  1                       11631
               /  /                                           /  /
         TGCCCCAGGCCTTGCCTCAGTATGCTGGCTCTGGAAACCTCACCCTGGCCCTTGAAGCGA
   961   ----------+---------+---------+---------+---------+---------+ 1020
         ACGGGGTCCGGAACGGAGTCATACGACCGAGACCTTTGGAGTGGGACCGGGAACTTCGCT

P  Q  A  L  P  Q  Y  A  G  S  G  N  L  T  A  L  E  A  K  -

S     BS
                               F     SC              H  D     A
                               A     TR              P  D     L
                               N     NF              H  E     U
                               1     11              1  1     1
                                      /
         AAACAGGAAAGTTGCATCAGGAAGTGAACCTGGTGGTGATGAGAGCCACTCAGCTCCAGA
  1021   ----------+---------+---------+---------+---------+---------+ 1080
         TTTGTCCTTTCAACGTAGTCCTTCACTTGGACCACCACTACTCTCGGTGAGTCGAGGTCT

T  G  K  L  H  Q  E  V  N  L  V  V  M  R  A  T  Q  L  Q  K  -

PS        S
                  M          ADNNPA    DF    AM     DE    A
                  N          VRLLUU    DA    LN     DS    L
                  L          AAAAM9    EN    UL     EP    U
                  1          224416    11    11     11    1
                              /////     /     /      /
         AAAATTTGACCTGTGAGGTGTGGGACCCACCTCCCCTAAGCTGATGCTGAGCTTGAAAC
  1081   ----------+---------+---------+---------+---------+---------+ 1140
         TTTTAAACTGGACACTCCACACCCCTGGGTGGAGGGGATTCGACTACGACTCGAACTTTG

N  L  T  C  E  V  W  G  P  T  S  P  K  L  M  L  S  L  K  L  -

M                T              H           M     DM
                  N                A              P           N     DS
                  L                Q              A           L     ET
                  1                1              2           1     12
                                                                     /
         TGGAGAACAAGGAGGCAAAGGTCTCGAAGCGGGAGAAGCCGGTGTGGGTGCTGAACCCTG
  1141   ----------+---------+---------+---------+---------+---------+ 1200
         ACCTCTTGTTCCTCCGTTTCCAGAGCTTCGCCCTCTTCGGCCACACCCACGACTTGGGAC

E  N  K  E  A  K  V  S  K  R  E  K  P  V  W  V  L  N  P  E  -

H                  PS           H
                           F  D  M  I  A            ADPA         I
                           0  D  A  N  V            VRUU         N
                           K  E  E  F  A            AAM9         F
                           1  1  3  1  1            2216         1
                                                     ///
         AGGCGGGGATGTGGCAGTGTCTGCTGAGTGACTCGGGACAGGTCCTGCTGGAATCCAACA
  1201   ----------+---------+---------+---------+---------+---------+ 1260
         TCCGCCCCTACACCGTCACAGACGACTCACTGAGCCCTGTCCAGGACGACCTTAGGTTGT

A  G  M  W  Q  C  L  L  S  D  S  G  Q  V  L  L  E  S  N  I  -

S        SA  BHF BS                          B
```

TABLE 5-continued

```
                     ANA      HNCP    SGNMAANXA             SH
                     VLU      PCRA    PIUNMULHV             PP
                     AA9      AIFL    1ADLH3ADA             1H
                     236      2111    21211A421             21
                      //       //      / / / /
     TCAAGGTTCTGCCCACATGGTCCACCCCGGTGCACGCGGATCCCGAGGGTGAGTGTGCCC
1261 ----------+----------+----------+----------+----------+----------+ 1320
     AGTTCCAAGACGGGTGTACCAGGTGGGGCCACGTGCGCCTAGGGCTCCCACTCACACGGG

K  V  L  P  T  W  S  T  P  V  H  A  D  P  E

BS  S      S       S
      MF              SC  F    DHNA     HNC       A  M  M
      A0              TR  A    RALU     PCR       F  A  B
      EK              NF  N    AEA9     AIF       L  E  0
      11              11  1    2346     211       3  2  2
       /              /   /     /        /
     TAGAGTAGCCTGCATCCAGGGACAGGCCCCAGCCGGGTGCTGACACGTCCACCTCCATCT
1321 ----------+----------+----------+----------+----------+----------+ 1380
     ATCTCATCGGACGTAGGTCCCTGTCCGGGGTCGGCCCACGACTGTGCAGGTGGAGGTAGA

BS       S
      M  D              M   SC  M  ANA  M                 M     S
      N  D              N   TR  B  VLU  B                 N     T
      L  E              L   NF  0  AA9  0                 L     Y
      1  1              1   11  2  246  2                 1     1
                              /        /
     CTTCCTCAGCACCTGAACTCCTGGGGGACCGTCAGTCTTCCTCTTCCCCCCAAAACCCA
1381 ----------+----------+----------+----------+----------+----------+ 1440
     GAAGGAGTCGTGGACTTGAGGACCCCCCTGGCAGTCAGAAGGAGAAGGGGGGTTTTGGGT

A  P  E  L  L  G  G  P  S  V  F  L  F  P  P  K  P  K  -

S           SS          N
           AN      M   HMANNAC  DM    M         NS             M
           UL      N   PNVCLUR  DS    A         LP             A
           3A      L   ALAIA9F  ET    E         AH             E
           A3      1   2121461  12    3         31             2
                          / / //    /                /
     AGGACACCCTCATGATCTCCCGGACCCCTGAGGTCACATGCGTGGTGGTGGACGTGAGCC
1441 ----------+----------+----------+----------+----------+----------+ 1500
     TCCTGTGGGAGTACTAGAGGGCCTGGGGACTCCAGTGTACGCACCACCACCTGCACTCGG

D  T  L  M  I  S  R  T  P  E  V  T  C  V  V  V  D  V  S  H  -

M     DM   M                RM    M
            N     DS   B                SA    N
            L     ET   0                AE    L
            1     12   2                12    1
                   /
     ACGAAGACCCTGAGGTCAAGTTCAACTGGTACGTGGACGGCGTGGAGGTGCATAATGCCA
1501 ----------+----------+----------+----------+----------+----------+ 1560
     TGCTTCTGGGACTCCAGTTCAAGTTGACCATGCACCTGCCGCACCTCCACGTATTACGGT

E  D  P  E  V  K  F  N  W  Y  V  D  G  V  E  V  H  N  A  K  -

F   FN                     S
           M      N   NSS             R      M   R   HNC  HH
           N      U   UPA             S      A   S   PCR  GP
           L      4   DBC             A      E   A   AIF  AH
           1      H   222             1      2   1   211  11
                       //                                   /
     AGACAAAGCCGCGGGAGGAGCAGTACAACAGCACGTACCGGGTGGTCAGCGTCCTCACCG
1561 ----------+----------+----------+----------+----------+----------+ 1620
     TCTGTTTCGGCGCCCTCCTCGTCATGTTGTCGTGCATGGCCCACCAGTCGCAGGAGTGGC

T  K  P  R  E  E  Q  Y  N  S  T  Y  R  V  V  S  V  L  T  V  -

BS
           M       SC                R
           N       TR                S
           L       NF                A
           1       11                1
                    /
     TCCTGCACCAGGACTGGCTGAATGGCAAGGAGTACAAGTGCAAGGTCTCCAACAAAGCCC
1621 ----------+----------+----------+----------+----------+----------+ 1680
     AGGACGTGGTCCTGACCGACTTACCGTTCCTCATGTTCACGTTCCAGAGGTTGTTTCGGG

L  H  Q  D  W  L  N  G  K  E  Y  K  C  K  V  S  N  K  A  L  -
```

TABLE 5-continued

```
                                              P S          S
          M   T                             A D N N P M A    A
          N   A                             V R L L U N U    U
          L   Q                             A A A A M L 9    9
          1   1                             2 2 4 4 1 1 6    6
                                             / / / /   /
     TCCCAGCCCCCATCGAGAAAACCATCTCCAAAGCCAAAGGTGGGACCCGTGGGGTGCGAG
1681 ----------+---------+---------+---------+---------+---------+ 1740
     AGGGTCGGGGGTAGCTCTTTTGGTAGAGGTTTCGGTTTCCACCCTGGGCACCCCACGCTC

P   A   P   I   E   K   T   I   S   K   A   K

S                        N
       H M   N       H H N   B S A H         D M   M   S   R
       A N   L       A P A   G F U A         D N   A   P   S
       E L   A       E A E   L I 9 E         E L   E   B   A
       3 1   3       3 2 1   1 1 6 3         1 1   3   2   1
                               /
     GGCCACATGGACAGAGGCCGGCTCGGCCCACCCTCTGCCCTGAGAGTGACCGCTGTACCA
1741 ----------+---------+---------+---------+---------+---------+ 1800
     CCGGTGTACCTGTCTCCGGCCGAGCCGGGTGGGAGACGGGACTCTCACTGGCGACATGGT

F                                      S S
           M   N   A   B           R   F               A H N N C C
           N   U   V   B           S   0               V P C C R R
           L   4   A   V           A   K               A A I I F F
           1   H   1   1           1   1               1 2 1 1 1 1
                                                         / / / /
     ACCTCTGTCCTACAGGGCAGCCCCGAGAACCACAGGTGTACACCCTGCCCCCATCCCGGG
1801 ----------+---------+---------+---------+---------+---------+ 1860
     TGGAGACAGGATGTCCCGTCGGGGCTCTTGGTGTCCACATGTGGGACGGGGGTAGGGCCC

G   Q   P   R   E   P   Q   V   Y   T   L   P   P   S   R   D   -

B S              B S   B
       S   A   F       S C              S C   S
       M   L   0       T R              T R   P
       A   U   K       N F              N F   M
       1   1   1       1 1              1 1   1
       /               /                /
     ATGAGCTGACCAAGAACCAGGTCAGCCTGACCTGCCTGGTCAAAGGCTTCTATCCCAGCG
1861 ----------+---------+---------+---------+---------+---------+ 1920
     TACTCGACTGGTTCTTGGTCCAGTCGGACTGGACGGACCAGTTTCCGAAGATAGGGTCGC

E   L   T   K   N   Q   V   S   L   T   C   L   V   K   G   F   Y   P   S   D   -
                                           F
                                           N H       B
                                           U P       B
                                           4 A       V
                                           H 2       1
     ACATCGCCGTGGAGTGGGAGAGCAATGGGCAGCCGGAGAACAACTACAAGACCACGCCTC
1921 ----------+---------+---------+---------+---------+---------+ 1980
     TGTAGCGGCACCTCACCCTCTCGTTACCCGTCGGCCTCTTGTTGATGTTCTGGTGCGGAG

I   A   V   E   W   E   S   N   G   Q   P   E   N   N   Y   K   T   T   P   P   -
               H                                                   B
       M I   M       N               H           M A                 S
       N N   B       L               P           N L                 P
       L F   0       A               H           L U                 M
       1 1   2       4               1           1 1                 1
     CCGTGCTGGACTCCGACGGCTCCTTCTTCCTCTACAGCAAGCTCACCGTGGACAAGAGCA
1981 ----------+---------+---------+---------+---------+---------+ 2040
     GGCACGACCTGAGGCTGCCGAGGAAGAAGGAGATGTCGTTCGAGTGGCACCTGTTCTCGT

V   L   D   S   D   G   S   F   F   L   Y   S   K   L   T   V   D   K   S   R   -
           F                         S
           N M       M B X       N F   M       N N
           U B       A B N       L A   N       S L
           4 0       E V N       A N   L       I A
           H 2       2 1 1       3 1   1       1 3
                                   /
     GGTGGCAGCAGGGGAACGTCTTCTCATGCTCCGTGATGCATGAGGCTCTGCACAACCACT
2041 ----------+---------+---------+---------+---------+---------+ 2100
     CCACCGTCGTCCCCTTGCAGAAGAGTACGAGGCACTACGTACTCCGAGACGTGTTGGTGA
```

TABLE 5-continued

```
    W   Q   Q   G   N   V   F   S   C   S   V   M   H   E   A   L   H   N   H   Y   -
                                    S
                        M   M   HNC                 CXH
                        B   N   PCR                 FMA
                        0   L   AIF                 RAE
                        2   1   211                 133
                                    /                   /
        ACACGCAGAAGAGCCTCTCCCTGTCTCCGGGTAAATGAGTGCGACGGCCG
2101    ----------+----------+----------+----------+----------+           2150
        TGTGCGTCTTCTCGGAGAGGGACAGAGGCCCATTTACTCACGCTGCCGGC

T   Q   K   S   L   S   L   S   P   G   K   *
```

Example 2
Preparation of the Fusion Proteins from Supernatants of COS Cells

COS cells grown in DME medium supplemented with 10% Calf Serum and gentamicin sulfate at 15 µg/ml were split into DME medium containing 10% NuSerum (Collaborative Research) and gentamicin to give 50% confluence the day before transfection. The next day, CsCl purified plasmid DNA was added to a final concentration of 0.1 to 2.0 µg/ml followed by DEAE Dextran to 400 µg/ml and chloroquine to 100 µM. After 4 hours at 37° C., the medium was aspirated and a 10% solution of dimethyl sulfoxide in phosphate buffered saline was added for 2 minutes, aspirated, and replaced with DME/10% Calf Serum. 8 to 24 hours later, the cells were trypsinized and split 1:2.

For radiolabeling, the medium was aspirated 40 to 48 hours after transfection, the cells washed once with phosphate buffered saline, and DME medium lacking cysteine or methionine was added. 30 minutes later, $^{35}$S-labeled cysteine and methionine were added to final concentrations of 30–60 µci and 100–200 µci respectively, and the cells allowed to incorporate label for 8 to 24 more hours. The supernatants were recovered and examined by electrophoresis on 7.5% polyacrylamide gels following denaturation and reduction, or on 5% polyacrylamide following denaturation without reduction. The CD4Bγ1 protein gave the same molecular mass with or without reduction, while the CD4Eγ1 and CD4Hγ1 fusion proteins showed molecular masses without reduction of twice the mass observed with reduction, indicating that they formed dimer structures. The CD4 IgM fusion proteins formed large multimers beyond the resolution of the gel system without reduction, and monomers of the expected molecular mass with reduction.

Unlabeled proteins were prepared by allowing the cells to grow for 5 to 10 days post transfection in DME medium containing 5% NuSerum and gentamicin as above. The supernatants were harvested, centrifuged, and purified by batch adsorption to either protein A trisacryl, protein A agarose, goat anti-human IgG antibody agarose, rabbit anti-human IgM antibody agarose, or monoclonal anti-CD4 antibody agarose. Antibody agarose conjugates were prepared by coupling purified antibodies to cyanogen bromide activated agarose according to the manufacturer's recommendations, and using an antibody concentration of 1 mg/ml. Following batch adsorption by shaking overnight on a rotary table, the beads were harvested by pouring into a sintered glass funnel and washed a few times on the funnel with phosphate buffered saline containing 1% Nonidet P40 detergent. The beads were removed from the funnel and poured into a small disposable plastic column (Quik-Sep QS-Q column, Isolab), washed with at least 20 column volumes of phosphate buffered saline containing 1% Nonidet P40, with 5 volumes of 0.15 M NaCl, 1 mM EDTA (pH 8.0), and eluted by the addition of either 0.1 M acetic acid, 0.1 M acetic acid containing 0.1 M NaCl, or 0.25 M glycine-HCl buffer, pH 2.5.

Example 3
Blockage of Syncytium Formation by the Fusion Proteins

Purified or partially purified fusion proteins were added to HPB-ALL cells infected 12 hours previously with a vaccinia virus recombinant encoding HIV envelope protein. After incubation for 6–8 more hours, the cells were washed with phosphate buffered saline, fixed with formaldehyde, and photographed. All of the full-length CD4 immunoglobulin fusion proteins showed inhibition of syncytium formation at a concentration of 20 µg/ml with the exception of the 4Hγ1 protein, which was tested only at 5 µg/ml and showed partial inhibition of syncytium formation under the same conditions.

Example 4
Chromium Release Cytolysis Assay

The purified fusion proteins were examined for ability to fix complement in a chromium release assay using vaccinia virus infected cells as a model system. Namalwa (B cell) or HPB-ALL (T cell) lines were infected with vaccinia virus encoding HIV envelope protein, and 18 hours later were radiolabeled by incubation in 1 mci/ml sodium $^{51}$chromate in phosphate buffered saline for 1 hour at 37°. The labeled cells were centrifuged to remove the unincorporated chromate, and incubated in microtiter wells with serial dilutions of the CD4 immunoglobulin fusion proteins and rabbit complement at a final concentration of 40%. After 1 hour at 37°, the cells were mixed well, centrifuged, and the supernatants counted in a gamma-ray counter. No specific release could be convincingly documented.

Example 5
Binding of the CD4Eγ1 Protein to Fc Receptors

Purified CD4Eγ1 fusion protein was tested for its ability to displace radiolabeled human IgG1 from human Fc receptors expressed on COS cells in culture. The IgG1 was radiolabeled with sodium $^{125}$iodide using 1 mci of iodide, 100 µg of IgG1, and two idobeads (Pierce). The labeled protein was separated from unincorporated counts by passage over a Sephadex G25 column equilibrated with phosphate buffered saline containing 0.5 mM EDTA and 5% nonfat milk. Serial dilutions of the CD4Eγ1 fusion protein or unlabeled IgG1 were prepared and mixed with a constant amount of radiolabeled IgG1 tracer. After incubation with COS cells bearing the FcRI and RcRII receptors at 4° C. for at least 45 minutes in a volume of 20 µl, 200 µl of a 3:2 mixture of dibutyl to dioctyl phthalates were added, and the cells separated from the unbound label by centrifugation in a microcentrifuge for 15 to 30 seconds. The tubes were cut with scissors, and the cell pellets counted in a gamma-ray counter. The affinity of the CD4Eγ1 protein for receptors was measured in parallel with the affinity of the authentic IgG1 protein, and was found to be the same, within experimental error.

Example 6
Stable Expression of the Fusion Construct pCD4Eγ1 in Baby Hamster Kidney Cells Twenty-four hours before transfection, $0.5 \times 10^6$ baby hamster kidney cells (BHK; ATCC CCL10) were seeded in a 25 cm$^2$ culture flask in Dulbecco's modified Eagle's medium (DMEM) containing 10% of fetal calf serum (FCS). The cells were cotransfected with a mixture of the plasmids pCD4Eγ1 (20 μg), pSV2dhfr (5 μg; Lee et al., *Nature* 294:228–232 (1981)) and pRMH140 (5 μg, Hudziak et al., *Cell* 31:137–146 (1982)) according to a modified calcium phosphate transfection technique as described in Zettlmeissl et al. (*Behring Inst. Res. Comm.* 82:26–34 (1988)). 72 h post-transfection, cells were split 1:3 to 1:4 (60 mm culture dishes) and resistant colonies were selected in DMEM medium containing 10% FCS, 400 μg/ml G418 (Geneticin, Gibco) and 1 μM methotrexate (selection medium). The medium was changed twice a week. The resistant colonies (40–100/transfection) appeared 10–15 day post-transfection and were further propagated either as a mixture of clones (i.e., BHK-MK1) or as individually isolated clones. For the determination of the relative expression levels, clone mixtures or individual clones were grown to confluency in T25 culture flasks, washed twice with protein-free DMEM medium, and incubated for 24 h with 5 ml protein-free DMEM medium. These media were collected and subjected to a human IgG specific ELISA in order to determine the relative expression levels of the CD4-IgG1 fusion protein CD4Eγ1. For further analysis an individual clone (BHK-UC3) was chosen due to its high relative expression levels.

Example 7
Detection of the CD4Eγ1 Protein in Culture Supernatants

For $^{35}$S methionine labeling of cells, the clone BHK-UC3 and untransfected BHK cells (control) were grown to confluency in T25 culture flasks and subsequently incubated for two hours in HamF12 medium without methionine. Labeling was achieved by incubating 24 h in 2.5 ml of the same medium containing 100 μCi $^{35}$S methionine (1070 Ci/mmole, Amersham). For the preparation of cell lysates, the labeled cells were harvested in 1 ml of phosphate buffered saline, pH 7.2 (PBS) and lysed by repetitive freezing and thawing. Cleared lysates (after centrifugation 20000 rpm, 20 min) and culture supernatants were incubated with Protein A-Sepharose (Pharmacia) and the bound material was analyzed on a 10% SDS-Protein A-Sepharose (Pharmacia) and the bound material was analyzed on a 10% SDS-gel according to Laemmli (*Nature* 227:680–685 (1970)), which was subsequently autoradiographed. A specific band of about 80 KDa can be detected only in the supernatant of clone BHK-UC3, which is absent in the lysate of clone BHK-UC3 and in the respective controls.

Example 8
Purification of the Protein CD4Eγ1 from Culture Supernatants

In order to demonstrate that the fusion protein coded by the plasmid pCD4Eγ1 can be obtained in high quantities, the clone BHK-UC3 was grown in 1750 cm$^2$ roller bottles in selection medium (500 ml). Confluent monolayers were washed twice with protein-free DMEM medium (200 ml) and further incubated for 48 h with protein-free DMEM medium (500 ml). The conditioned culture supernatants (1–2 l) and respective supernatants from untransfected BHK cells were cleared by centrifugation (9000 rpm, 30 min) and microfiltered through a 0.45 μm membrane (Nalgene). After addition of 1% (v/v) of 1.9 M Tris-HCl buffer, pH 8.6, the conditioned medium was absorbed to a Protein A-Sepharose column equilibrated with 50 mM Tris-HCl pH 8.6 buffer containing 150 mM NaCl (4° C.). The loaded column was washed with 10 column volumes of equilibration buffer. Elution of the CD4-IgG1 fusion protein CD4Eγ1 was achieved with 0.1 M sodium citrate buffer, pH 3, followed by immediate neutralization of the column efflux to pH 8 by Tris-base. The peak fractions were pooled, and the pool was analyzed on a Coomassie blue stained SDS-gel resulting in a band of the expected size (80 KDa), and which reacted with a polyclonal anti-human IgG heavy chain antibody and a mouse monoclonal anti-CD4 antibody (BMA040, Behringwerke) in Western Blots. The yields of purified fusion proteins obtained by the given procedure is 5–18 mg/24 h/l culture supernatant. The respective value for a BHK clone mixture (about 80 resistant clones; BHK-MK1) as described above was 2–3 mg/24 h/l.

Example 9
Physical and Biological Characterization of the CD4Eγ1 Fusion Protein

As proven by SDS-electrophoresis on 10–15% gradient gels (Phast-System, Pharmacia) under non-reductive conditions, the CD4Eγ1 fusion protein migrates at the position of a homodimer (about 160 KDa) like a non-reduced mouse monoclonal antibody. This result is supported by analytical equilibrium ultracentrifugation, where the fusion protein behaves as a homogeneous dimeric molecule of about 150 KDa. The absorbance coefficient of the protein was determined as $A_{280}=18$ cm$^2$/mg using the quantitative protein determination according to Bradford (*Anal. Biochem.* 72:248–254 (1976)).

The CD4Eγ1-fusion protein shows specific complex formation with a solubilized βgal-gp120 fusion protein (pMB1790; Broker et al., *Behring Inst. Res. Commun.* 82:338–348 (1988)) expressed in *E. coli*. In this protein (110 KDa), a major part of the HIV gp120 protein (Val$_{49}$-Trp$_{646}$) is fused to f-galactosidase (amino acids 1–375). In a control experiment a 67-KDa βgal-HIV 3'orf fusion protein (βgal1–375; 3'orf Pro14-Asp123) showed no complex formation. In these experiments, the CD4Eγ1-protein was incubated with the respective fusion protein in molar rations of about 5:1. The complex was isolated by binding to Protein A-Sepharose and the Protein A-Sepharose bound proteins—together with relevant controls—were analyzed on 10–15% gradient SDS-gels (Phast-System, Pharmacia).

The CD4Eγ1 fusion protein binds to the surface of HIV (HIV1/HTLV-IIIB) infected cultured T4-lymphocytes as determined by direct immunofluorescence with fluorescein-isothiocyanate (FITC) labeled CD4Eγ1 protein. It blocks syncytia formation in cultured T4-lymphocytes upon HIV infection (0.25 TCID/cell) at a concentration of 10 μg/ml. Furthermore, HIV-infected cultured T4-lymphocytes (subclone of cell line H9) are selectively killed upon Incubation with CD4Eγ1 in the presence or absence of complement: To a highly (>50%) HIV infected culture of T4-lymphocytes (10$^6$ cells/ml) 50, 10 or 1 μg/ml CD4Eγ1 fusion protein was added in the presence or absence of guinea pig complement. Cells were observed for specific killing by the fusion protein, which is defined by the percentage of killed cells after 3 days in relation to viable cells in the culture at the beginning of the experiment corrected by the values for unspecific killing observed in control cultures, lacking the CD4Eγ1 fusion protein (Table 5, Experiment I). Surprisingly, addition of CD4Eγ1 protein to the infected T4 cells in the absence of complement resulted in similar specific killing rates as in the presence of complement (Table 5, Experiment II). This result demonstrates a complement independent cytolytic effect of CD4Eγ1 on HIV infected T-lymphocytes in culture.

TABLE 5

| No. Experiment | Assay System | Specific Killing (%) |
|---|---|---|
| I | non-infected T4-cells + 50 μg/ml CD4Eγ1 + Compl. | 0.7 |
|  | infected T4-cells + 50 μg/ml CD4Eγ1 + Compl. | 35.1 |
|  | infected T4-cells + 10 μg/ml CD4Eγ1 + Compl. | 25.1 |
|  | infected T4-cells + 1 μg/ml CD4Eγ1 + Compl. | 25 |
| II | infected T4-cells + 10 μg/ml CD4Eγ1 + Compl. | 49.9 |
|  | infected T4-cells + 10 μg/ml CD4Eγ1 + Compl. | 69.4 |

Having now fully described this invention, it will be appreciated by those skilled In the art that the same can be performed with any wide range of equivalent parameters of composition, conditions, and methods of preparing such fusion proteins without departing from the spirit or scope of the invention or any embodiment thereof.

What is claimed is:

1. A nucleic acid molecule encoding a fusion protein comprising 1) a DNA sequence encoding amino acids 1–173 of CD4, and 2) a DNA sequence encoding an immunoglobulin heavy chain, wherein the DNA sequence which encodes at least the variable region of said immunoglobulin chain has been replaced with the DNA sequence which encodes amino acids 1–173 of CD4, whereby a nucleic acid molecule encoding a fusion protein capable of being secreted is formed.

2. The fusion protein gene of claim 1, wherein said immunoglobulin chain is of the class IgM, IgG1 or IgG3.

3. A vector comprising the nucleic acid molecule of claim 1.

4. A host cell transformed with the vector of claim 3.

5. The host cell of claim 4 which expresses an immunoglobulin light chain together with the expression product of said fusion protein gene.

6. A method of producing a fusion protein which is capable of being secreted comprising extracellular CD4 through amino acid 173 of CD4, which fusion protein binds to gp120, and an immunoglobulin heavy chain, wherein at least the variable region of the immunoglobulin chain has been substituted with extracellular CD4 through amino acid 173, which binds to HIV or SIV gp120, which comprises cultivating in a nutrient medium under protein-producing conditions, a host strain transformed with the vector of claim 3, said vector further comprising expression signals which are recognized by said host strain and direct expression of said fusion protein, and recovering the fusion protein so produced.

7. The method of claim 6, wherein said host cell produces immunoglobulin light chains and said fusion protein comprises an immunoglobulin heavy chain of the class IgM, IgG1 or IgG3.

8. A nucleic acid molecule encoding a fusion protein comprising 1) a DNA sequence encoding amino acids 1–173 of CD4, and 2) a DNA sequence encoding an immunoglobulin light chain, where in the DNA sequence which encodes the variable region of said immunoglobulin light chain has been replaced with the DNA sequence which encodes amino acids 1–173 of CD4, whereby a nucleic acid molecule encoding a fusion protein capable of being secreted is formed.

9. A vector comprising the nucleic acid molecule of claim 8.

10. A host cell transformed with the vector of claim 9.

11. The host cell of claim 10 which expresses an immunoglobulin heavy chain together with the expression product of said fusion protein gene.

12. The host cell of claim 11, wherein said immunoglobulin heavy chain is of the immunoglobulin class IgM, IgG1 or IgG3.

13. A method of producing a fusion protein which is capable of being secreted comprising extracellular CD4, or fragment thereof which binds to gp120 when fused to an immunoglobulin chain, and an immunoglobulin light chain, wherein the variable region of the immunoglobulin chain has been substituted with extracellular CD4, or said fragment thereof which binds to HIV or SIV gp120, which comprises cultivating in a nutrient medium under protein-producing conditions, a host cell transformed with the vector of claim 9, said vector further comprising expression signals which are recognized by said host strain and direct expression of said fusion protein, and recovering the fusion protein so produced.

14. The method of claim 13, wherein said host cell produces immunoglobulin heavy chains of the class IgM, IgG1 or IgG3, together with said fusion protein.

* * * * *

UNITED STATES PATENT AND TRADEMARK OFFICE
CERTIFICATE OF CORRECTION

PATENT NO. : 6,004,781

DATED : December 21, 1999

INVENTOR(S) : Brian SEED

It is certified that error appears in the above-identified patent and that said Letters Patent is hereby corrected as shown below:

In Column 73, line 42, please delete "fusion protein gene" and replace with --nucleic acid molecule--.

Signed and Sealed this

Nineteenth Day of September, 2000

Attest:

Q. TODD DICKINSON

*Attesting Officer*

*Director of Patents and Trademarks*